(12) United States Patent
Inman et al.

(10) Patent No.: US 9,549,799 B2
(45) Date of Patent: Jan. 24, 2017

(54) SURGICAL KIT FOR SECURING AN IMPLANTABLE SLING IN A PUBIC REGION

(71) Applicant: AMS Research, LLC, Minnetonka, MN (US)

(72) Inventors: Mona J. Inman, Eden Prairie, MN (US); Kevin R. Arnal, Excelsior, MN (US); Matthew J. Monarski, Victoria, MN (US); Robert L. Rykhus, Jr., Edina, MN (US); Suranjan Roychowdhury, Plymouth, MN (US); Jeffrey A. Lechner-Riehle, Burnsville, MN (US); Eric S. Watschke, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 111 days.

(21) Appl. No.: 13/934,739

(22) Filed: Jul. 3, 2013

(65) Prior Publication Data
US 2013/0296641 A1    Nov. 7, 2013

Related U.S. Application Data

(63) Continuation of application No. 11/993,441, filed as application No. PCT/US2006/023956 on Jun. 20, 2006, now abandoned.
(Continued)

(51) Int. Cl.
*A61F 2/02* (2006.01)
*A61F 2/04* (2013.01)
(Continued)

(52) U.S. Cl.
CPC ......... *A61F 2/0045* (2013.01); *A61B 17/0401* (2013.01); *A61B 17/0487* (2013.01);
(Continued)

(58) Field of Classification Search
CPC .... A61F 2/0004; A61F 2/0031; A61F 2/0036; A61F 2/0045; A61F 2/0063; A61B 2017/00805; A61B 17/0487; A61B 2017/0404; A61B 2017/0446; A61B 2017/0454; A61B 2017/0456; A61B 2017/0458; A61B 2017/0459; A61B 2017/0461; A61B 2017/0462; A61B 2017/0488; A61B 2017/049
(Continued)

(56) References Cited

U.S. PATENT DOCUMENTS 2,738,790 A    3/1956    Todt et al.
3,472,232 A    10/1969   Earl
(Continued)

FOREIGN PATENT DOCUMENTS

AU    2002241673    11/2005
CA    2404459       8/2005
(Continued)

OTHER PUBLICATIONS

"Access Instrument System with AlloSling Fascia" (5 pages with two pages of Instructions for Use).
"We're staying ahead of the curve" Introducing the IVS Tunneller Device for Tension Free Procedures, Tyco Healthcare, 3 pages (2002).
(Continued)

*Primary Examiner* — Charles A Marmor, II
*Assistant Examiner* — Thaddeus Cox
(74) *Attorney, Agent, or Firm* — Brake Hughes Ballermann LLP

(57) ABSTRACT

Surgical procedures, kits and implants for alleviating human incontinence, and particularly providing improved methods and apparatus to secure a urethral sling (30) to pubic bone (24, 26) to support the urethra and alleviate incontinence are disclosed. Bone anchors (64) are driven into pubic bones with elongated bone anchor sutures (84) configured to be passed through openings of a urethral sling. Suture retainers
(Continued)

are applied to the sutures to apply retentive force to the urethral sling to maintain the fixation of the urethral sling proximate to the pubic bone.

14 Claims, 11 Drawing Sheets

Related U.S. Application Data

(60) Provisional application No. 60/692,667, filed on Jun. 21, 2005.

(51) Int. Cl.
  *A61B 17/04* (2006.01)
  *A61F 2/00* (2006.01)
  *A61B 17/00* (2006.01)
  *A61B 17/06* (2006.01)

(52) U.S. Cl.
  CPC ............... *A61B 2017/00805* (2013.01); *A61B 2017/044* (2013.01); *A61B 2017/0446* (2013.01); *A61B 2017/0458* (2013.01); *A61B 2017/0462* (2013.01); *A61B 2017/06176* (2013.01)

(58) Field of Classification Search
  USPC ................................................ 600/29–30, 37
  See application file for complete search history.

(56) References Cited

U.S. PATENT DOCUMENTS

| | | |
|---|---|---|
| 3,580,313 A | 5/1971 | McKnight |
| 3,763,860 A | 10/1973 | Clarke |
| 3,858,783 A | 1/1975 | Kapitanov et al. |
| 3,976,079 A * | 8/1976 | Samuels ............ A61B 17/0466 24/115 M |
| 3,995,619 A | 12/1976 | Glatzer |
| 4,069,825 A * | 1/1978 | Akiyama ..................... 606/158 |
| 4,172,458 A | 10/1979 | Pereyra |
| 4,235,238 A | 11/1980 | Ogiu et al. |
| 4,441,497 A | 4/1984 | Paudler |
| 4,509,516 A | 4/1985 | Richmond |
| 4,548,202 A | 10/1985 | Duncan |
| 4,632,100 A | 12/1986 | Somers et al. |
| 4,873,976 A | 10/1989 | Schreiber |
| 4,932,962 A | 6/1990 | Yoon et al. |
| 4,938,760 A | 7/1990 | Burton et al. |
| 4,969,892 A | 11/1990 | Burton et al. |
| 4,979,956 A | 12/1990 | Silvestrini |
| 5,013,292 A | 5/1991 | Lemay |
| 5,013,316 A | 5/1991 | Goble et al. |
| 5,053,043 A | 10/1991 | Gottesman et al. |
| 5,085,661 A | 2/1992 | Moss |
| 5,112,344 A | 5/1992 | Petros |
| 5,141,520 A | 8/1992 | Goble et al. |
| 5,149,329 A | 9/1992 | Richardson |
| 5,188,636 A | 2/1993 | Fedotov |
| 5,209,756 A | 5/1993 | Seedhom et al. |
| 5,234,438 A | 8/1993 | Semrad |
| 5,256,133 A | 10/1993 | Spitz |
| 5,268,001 A | 12/1993 | Nicholson et al. |
| 5,269,783 A | 12/1993 | Sander |
| 5,281,237 A | 1/1994 | Gimpelson |
| 5,328,077 A | 7/1994 | Lou |
| 5,337,736 A | 8/1994 | Reddy |
| 5,354,292 A | 10/1994 | Braeuer et al. |
| 5,368,595 A | 11/1994 | Lewis |
| 5,370,650 A | 12/1994 | Tovey et al. |
| 5,370,661 A * | 12/1994 | Branch ..................... 606/232 |
| 5,370,662 A | 12/1994 | Stone et al. |
| 5,376,097 A | 12/1994 | Phillips |
| 5,383,904 A | 1/1995 | Totakura et al. |
| 5,403,328 A | 4/1995 | Shallman |
| 5,439,467 A | 8/1995 | Benderev et al. |
| 5,474,518 A | 12/1995 | Velazquez |
| 5,474,543 A | 12/1995 | McKay |
| 5,500,000 A * | 3/1996 | Feagin et al. .................. 606/232 |
| 5,520,700 A | 5/1996 | Beyar et al. |
| 5,520,703 A | 5/1996 | Essig |
| 5,527,342 A | 6/1996 | Pietrzak et al. |
| 5,544,664 A | 8/1996 | Benderev et al. |
| 5,562,689 A | 10/1996 | Green et al. |
| 5,571,139 A | 11/1996 | Jenkins, Jr. |
| 5,582,188 A | 12/1996 | Benderev et al. |
| 5,591,163 A | 1/1997 | Thompson |
| 5,591,206 A | 1/1997 | Moufarrege |
| 5,611,515 A | 3/1997 | Benderev et al. |
| 5,626,590 A * | 5/1997 | Wilk .................. A61B 17/0469 606/139 |
| 5,628,756 A | 5/1997 | Barker, Jr. et al. |
| 5,643,320 A | 7/1997 | Lower et al. |
| 5,669,935 A | 9/1997 | Rosenman et al. |
| 5,683,349 A | 11/1997 | Makower et al. |
| 5,690,655 A | 11/1997 | Hart et al. |
| 5,697,931 A | 12/1997 | Thompson |
| 5,709,708 A | 1/1998 | Thal |
| 5,725,529 A | 3/1998 | Nicholson et al. |
| 5,725,541 A | 3/1998 | Anspach, III et al. |
| 5,741,282 A | 4/1998 | Anspach, III et al. |
| 5,842,478 A | 12/1998 | Benderev et al. |
| 5,899,909 A | 5/1999 | Claren et al. |
| 5,904,692 A | 5/1999 | Steckel et al. |
| 5,922,026 A | 7/1999 | Chin |
| 5,925,047 A | 7/1999 | Errico et al. |
| 5,944,732 A | 8/1999 | Raulerson et al. |
| 5,954,057 A | 9/1999 | Li |
| 5,972,000 A | 10/1999 | Beyar et al. |
| 5,980,558 A | 11/1999 | Wiley |
| 5,984,927 A | 11/1999 | Wenstrom, Jr. et al. |
| 5,988,171 A | 11/1999 | Sohn et al. |
| 5,997,554 A | 12/1999 | Thompson |
| 6,015,428 A * | 1/2000 | Pagedas ..................... 606/232 |
| 6,027,523 A | 2/2000 | Schmieding |
| 6,030,393 A | 2/2000 | Corlew |
| 6,036,701 A | 3/2000 | Rosenman |
| 6,042,583 A | 3/2000 | Thompson et al. |
| 6,048,351 A | 4/2000 | Gordon et al. |
| 6,053,935 A | 4/2000 | Brenneman et al. |
| 6,056,688 A | 5/2000 | Benderev et al. |
| 6,099,538 A | 8/2000 | Moses |
| 6,127,597 A | 10/2000 | Beyar et al. |
| 6,168,611 B1 | 1/2001 | Risvi |
| 6,200,330 B1 | 3/2001 | Benderev et al. |
| 6,231,592 B1 * | 5/2001 | Bonutti et al. ................ 606/232 |
| 6,241,736 B1 | 6/2001 | Sater et al. |
| 6,245,082 B1 | 6/2001 | Gellman et al. |
| 6,264,676 B1 | 7/2001 | Gellman et al. |
| 6,273,852 B1 | 8/2001 | Lehe et al. |
| 6,322,492 B1 | 11/2001 | Kovac |
| 6,328,744 B1 | 12/2001 | Harari et al. |
| 6,334,446 B1 | 1/2002 | Beyar |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,423,080 B1 | 7/2002 | Gellman et al. |
| 6,451,024 B1 | 9/2002 | Thompson et al. |
| 6,475,139 B1 | 11/2002 | Miller |
| 6,478,727 B2 | 11/2002 | Scetbon |
| 6,491,703 B1 | 12/2002 | Ulmsten |
| 6,502,578 B2 | 1/2003 | Raz et al. |
| 6,506,190 B1 | 1/2003 | Walshe |
| 6,530,943 B1 | 3/2003 | Hoepffner et al. |
| 6,544,273 B1 | 4/2003 | Harari et al. |
| 6,582,443 B2 | 6/2003 | Cabak et al. |
| 6,592,515 B2 | 7/2003 | Thierfelder |
| 6,592,610 B2 | 7/2003 | Beyar |
| 6,596,001 B2 | 7/2003 | Stormby et al. |
| 6,599,235 B2 | 7/2003 | Kovac |
| 6,602,260 B2 | 8/2003 | Harari et al. |
| 6,612,977 B2 | 9/2003 | Staskin |

(56) References Cited

U.S. PATENT DOCUMENTS

| | | |
|---|---|---|
| 6,635,058 B2 | 10/2003 | Beyar et al. |
| 6,638,210 B2 | 10/2003 | Berger |
| 6,641,524 B2 | 11/2003 | Kovac |
| 6,641,525 B2 | 11/2003 | Rocheleau |
| 6,652,450 B2 | 11/2003 | Neisz et al. |
| 6,673,010 B2 | 1/2004 | Skiba et al. |
| 6,685,629 B2 | 2/2004 | Therin |
| 6,689,047 B2 | 2/2004 | Gellman |
| 6,730,110 B1 | 5/2004 | Harari et al. |
| 6,746,455 B2 | 6/2004 | Beyar et al. |
| 6,752,814 B2 | 6/2004 | Gellman et al. |
| 6,802,807 B2 | 10/2004 | Anderson |
| 6,843,796 B2 | 1/2005 | Harari et al. |
| 6,884,212 B2 | 4/2005 | Thierfelder et al. |
| 6,908,425 B2 | 6/2005 | Luscombe |
| 6,908,473 B2 | 6/2005 | Skiba et al. |
| 6,911,002 B2 | 6/2005 | Fierro |
| 6,911,003 B2 | 6/2005 | Anderson et al. |
| 6,932,759 B2 | 8/2005 | Kammerer |
| 6,936,052 B2 | 8/2005 | Gellman et al. |
| 6,971,986 B2 | 12/2005 | Staskin et al. |
| 6,974,462 B2 | 12/2005 | Sater |
| 6,981,983 B1 | 1/2006 | Rosenblatt et al. |
| 6,991,597 B2 | 1/2006 | Gellman et al. |
| 7,014,607 B2 | 3/2006 | Gellman |
| 7,025,772 B2 | 4/2006 | Gellman et al. |
| 7,037,255 B2 | 5/2006 | Inman |
| 7,048,682 B2 | 5/2006 | Neisz et al. |
| 7,056,333 B2 | 6/2006 | Walshe |
| 7,070,556 B2 | 7/2006 | Anderson |
| 7,083,637 B1 | 8/2006 | Tannhauser |
| 7,087,059 B2 | 8/2006 | Harari et al. |
| 7,112,171 B2 | 9/2006 | Rocheleau et al. |
| 7,121,997 B2 | 10/2006 | Kammerer et al. |
| 7,131,943 B2 | 11/2006 | Kammerer |
| 7,223,229 B2 | 5/2007 | Inman et al. |
| 7,226,407 B2 | 6/2007 | Kammerer |
| 7,226,408 B2 | 6/2007 | Harai et al. |
| 7,229,404 B2 | 6/2007 | Bouffier |
| 7,229,453 B2 | 6/2007 | Anderson et al. |
| 7,235,043 B2 | 6/2007 | Gellman et al. |
| 7,261,723 B2 | 8/2007 | Smith et al. |
| 7,267,645 B2 | 9/2007 | Anderson et al. |
| 7,291,104 B2 | 11/2007 | Neisz et al. |
| 7,297,102 B2 | 11/2007 | Smith et al. |
| 7,303,525 B2 | 12/2007 | Watschke et al. |
| 7,326,213 B2 | 2/2008 | Benderev et al. |
| 7,347,812 B2 | 3/2008 | Mellier |
| 7,351,196 B2 | 4/2008 | Goldmann et al. |
| 7,351,197 B2 | 4/2008 | Montpetit et al. |
| 7,357,773 B2 | 4/2008 | Watschke et al. |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,407,480 B2 | 8/2008 | Staskin |
| 7,410,460 B2 | 8/2008 | Benderev |
| 7,413,540 B2 | 8/2008 | Gellman et al. |
| 7,422,557 B2 | 9/2008 | Arnal |
| 7,494,495 B2 | 2/2009 | Delorme et al. |
| 7,500,945 B2 | 3/2009 | Cox |
| 7,517,313 B2 | 4/2009 | Thierfelder et al. |
| 7,527,588 B2 | 5/2009 | Zaddem et al. |
| 7,527,633 B2 | 5/2009 | Rioux |
| 7,547,316 B2 | 6/2009 | Priewe et al. |
| 7,588,598 B2 | 9/2009 | Delorme et al. |
| 7,601,118 B2 | 10/2009 | Smith et al. |
| 7,614,999 B2 | 11/2009 | Gellman et al. |
| 7,637,860 B2 | 12/2009 | MacLean |
| 7,686,759 B2 | 3/2010 | Sater |
| 7,686,760 B2 | 3/2010 | Anderson et al. |
| 7,691,050 B2 | 4/2010 | Gellman et al. |
| 7,691,052 B2 | 4/2010 | Gellman et al. |
| 7,740,576 B2 | 6/2010 | Hodroff |
| 7,753,839 B2 | 7/2010 | Siegel et al. |
| 7,762,942 B2 | 7/2010 | Neisz et al. |
| 2001/0000533 A1* | 4/2001 | Kovac ................ A61F 2/0045 606/232 |
| 2001/0018549 A1 | 8/2001 | Scetbon |
| 2001/0041895 A1 | 11/2001 | Beyar et al. |
| 2001/0049467 A1 | 12/2001 | Lehe et al. |
| 2001/0053916 A1 | 12/2001 | Rioux |
| 2002/0007222 A1 | 1/2002 | Desai |
| 2002/0028980 A1 | 3/2002 | Thierfelder et al. |
| 2002/0055748 A1 | 5/2002 | Gellman et al. |
| 2002/0058959 A1 | 5/2002 | Gellman et al. |
| 2002/0068948 A1 | 6/2002 | Stormby et al. |
| 2002/0077526 A1 | 6/2002 | Kammerer et al. |
| 2002/0082619 A1 | 6/2002 | Cabak et al. |
| 2002/0091373 A1 | 7/2002 | Berger |
| 2002/0095163 A1* | 7/2002 | Beyar ........................... 606/139 |
| 2002/0107525 A1 | 8/2002 | Harari et al. |
| 2002/0147382 A1 | 10/2002 | Neisz et al. |
| 2002/0151909 A1 | 10/2002 | Gellman et al. |
| 2002/0156487 A1 | 10/2002 | Gellman et al. |
| 2002/0156488 A1 | 10/2002 | Gellman et al. |
| 2002/0161382 A1 | 10/2002 | Neisz |
| 2002/0183762 A1 | 12/2002 | Anderson et al. |
| 2002/0188169 A1 | 12/2002 | Kammerer et al. |
| 2003/0004395 A1 | 1/2003 | Therin |
| 2003/0009181 A1 | 1/2003 | Gellman et al. |
| 2003/0023136 A1 | 1/2003 | Raz |
| 2003/0023138 A1 | 1/2003 | Luscombe |
| 2003/0036676 A1 | 2/2003 | Scetbon |
| 2003/0045774 A1 | 3/2003 | Staskin et al. |
| 2003/0050530 A1 | 3/2003 | Neisz et al. |
| 2003/0065402 A1 | 4/2003 | Anderson et al. |
| 2003/0088270 A1* | 5/2003 | Lubbers et al. ............. 606/213 |
| 2003/0176875 A1 | 9/2003 | Anderson |
| 2004/0015057 A1 | 1/2004 | Rocheleau et al. |
| 2004/0193215 A1* | 9/2004 | Harari et al. ................ 606/213 |
| 2004/0225181 A1 | 11/2004 | Chu et al. |
| 2004/0267088 A1 | 12/2004 | Kammerer |
| 2005/0000424 A1 | 1/2005 | Itsukaichi et al. |
| 2005/0000523 A1 | 1/2005 | Beraud |
| 2005/0004576 A1 | 1/2005 | Benderev |
| 2005/0055104 A1 | 3/2005 | Arnal et al. |
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt et al. |
| 2006/0058578 A1 | 3/2006 | Browning |
| 2006/0089524 A1 | 4/2006 | Chu |
| 2006/0089525 A1 | 4/2006 | Mamo et al. |
| 2006/0190041 A1* | 8/2006 | Fallin ................ A61B 17/0401 606/232 |
| 2006/0195007 A1 | 8/2006 | Anderson |
| 2006/0229493 A1 | 10/2006 | Weiser et al. |
| 2006/0229596 A1 | 10/2006 | Weiser et al. |
| 2006/0252980 A1 | 11/2006 | Arnal et al. |
| 2006/0287571 A1 | 12/2006 | Gozzi |
| 2007/0015953 A1 | 1/2007 | MacLean |
| 2007/0078295 A1 | 4/2007 | landgrebe |
| 2007/0173864 A1 | 7/2007 | Chu |
| 2008/0039678 A1 | 2/2008 | Montpetit et al. |
| 2008/0300607 A1 | 12/2008 | Meade et al. |
| 2009/0012353 A1 | 1/2009 | Beyer |
| 2009/0221867 A1 | 9/2009 | Ogdahl et al. |
| 2009/0221868 A1 | 9/2009 | Evans |

FOREIGN PATENT DOCUMENTS

| | | |
|---|---|---|
| DE | 2305815 | 2/1973 |
| DE | 4220283 C2 | 5/1994 |
| DE | 10211360 | 9/2003 |
| DE | 20016866 | 3/2007 |
| EP | 0650703 A1 | 6/1994 |
| EP | 0643945 A2 | 7/1994 |
| EP | 0632999 A1 | 1/1995 |
| EP | 1093758 A1 | 4/2001 |

(56) References Cited

FOREIGN PATENT DOCUMENTS

| | | |
|---|---|---|
| EP | 1342450 B1 | 9/2003 |
| FR | 2852813 A1 | 1/2004 |
| GB | 2268690 A | 1/1994 |
| GB | 2353220 A | 10/2000 |
| SU | 1225547 A1 | 4/1986 |
| WO | WO9319678 A2 | 10/1993 |
| WO | WO9511631 A1 | 5/1995 |
| WO | WO9525469 A1 | 9/1995 |
| WO | WO9716121 A1 | 5/1997 |
| WO | WO9730638 A1 | 8/1997 |
| WO | WO9747244 A1 | 12/1997 |
| WO | WO9819606 A1 | 5/1998 |
| WO | WO9835606 A1 | 8/1998 |
| WO | WO9835616 A1 | 8/1998 |
| WO | WO9842261 A1 | 10/1998 |
| WO | WO9853746 A1 | 12/1998 |
| WO | WO9937217 A1 | 7/1999 |
| WO | WO9952450 A1 | 10/1999 |
| WO | WO9953844 A1 | 10/1999 |
| WO | WO9959477 A1 | 11/1999 |
| WO | WO0013601 A1 | 3/2000 |
| WO | WO0040158 A2 | 7/2000 |
| WO | WO0074594 A1 | 12/2000 |
| WO | WO0074613 A1 | 12/2000 |
| WO | WO0074633 A2 | 12/2000 |
| WO | O0232284 A2 | 4/2002 |
| WO | WO0230293 A1 | 4/2002 |
| WO | WO0234124 A2 | 5/2002 |
| WO | WO0239890 A2 | 5/2002 |
| WO | O02058563 A1 | 8/2002 |
| WO | WO02062237 A1 | 8/2002 |
| WO | O02071953 A2 | 9/2002 |
| WO | WO02069781 | 9/2002 |
| WO | WO03013392 A2 | 2/2003 |
| WO | WO03017848 A1 | 3/2003 |
| WO | WO03047435 A1 | 6/2003 |
| WO | WO03068107 A1 | 8/2003 |
| WO | WO03075792 A1 | 9/2003 |
| WO | WO03086205 A2 | 10/2003 |
| WO | WO03092546 A2 | 11/2003 |
| WO | WO03096928 A1 | 11/2003 |
| WO | WO03096929 A1 | 11/2003 |
| WO | WO2004016196 A2 | 2/2004 |
| WO | WO2004034912 A1 | 4/2004 |
| WO | WO2005004727 A1 | 1/2005 |
| WO | WO2005046511 A2 | 5/2005 |
| WO | WO2005048850 A2 | 6/2005 |
| WO | WO2005079702 A1 | 9/2005 |
| WO | WO2005122954 A1 | 12/2005 |
| WO | WO2006007189 A1 | 1/2006 |
| WO | WO2006007190 A1 | 1/2006 |
| WO | WO2006031879 A1 | 3/2006 |
| WO | WO2006108145 A1 | 10/2006 |
| WO | WO2007002012 A1 | 1/2007 |
| WO | WO2007002071 A1 | 1/2007 |
| WO | WO2007014241 A1 | 2/2007 |
| WO | WO2007016083 A1 | 2/2007 |
| WO | WO2007027592 A2 | 3/2007 |
| WO | WO2007059199 A2 | 5/2007 |
| WO | WO2007097994 | 8/2007 |
| WO | WO2007137226 A2 | 11/2007 |
| WO | WO2007146784 A2 | 12/2007 |
| WO | WO2007149348 A2 | 12/2007 |
| WO | WO2008057261 A2 | 5/2008 |
| WO | WO2008124056 A1 | 10/2008 |
| WO | WO2009005714 A2 | 1/2009 |
| WO | WO2009017680 A2 | 2/2009 |

OTHER PUBLICATIONS

Advantage A/T™, Surgical Mesh Sling Kit, Boston Scientific, 6 pages (2002).
Benderev, Theodore V., MD, A Modified Percutaneous Outpatient Bladder Neck Suspension System, Journal of Urology, vol. 152, pp. 2316-2320 (Dec. 1994).
Benderev, Theodore V., MD, Anchor Fixation and Other Modifications of Endoscopic Bladder Neck Suspension, Urology, vol. 40, No. 5, pp. 409-418 (Nov. 1992).
Capio™ CL—Transvaginal Suture Capturing Device—Transvaginal Suture Fixation to Cooper's Ligament for Sling Procedures, Boston Scientific, Microvasive®, 8 pages, (2002).
Cook/Ob Gyn®, Urogynecology, Copyright Cook Urological Inc., pp. 1-36 (1996).
Dargent, D. et al., Insertion of a Suburethral Sling Through the Obturator Membrane in the Treatment of Female Urinary Incontinence, Gynecol Obstet Fertil, vol. 30, pp. 576-582 (2002).
Gynecare TVT Tension-Free Support for Incontinence, The tension-free solution to female Incontinence, Gynecare Worldwide,6 pages, (2002).
Intramesh® L.I.F.T.® Polypropylene Less Invasive Free Tape, Cousin Biotech, 2 pages (no date).
IVS Tunneller—A Universal instrument for anterior and posterior intra-vaginal tape placement, Tyco Healthcare, 4 pages (Aug. 2002).
IVS Tunneller—ein universelles Instrument fur die Intra Vaginal Schlingenplastik, Tyco Healthcare, 4 pages (2001).
IVS Tunneller, AMA, (no date) 4 pages.
IVS Tunneller, Australian Medical Design Breakthrough for GSI, mixed incontinence and vault prolapse, AMA Medical Products, 4 pages (no date).
Karram, Mickey M. et al., Chapter 19 Surgical Treatment of Vaginal Vault Prolapse, Urogynecology and Reconstructive Pelvic Surgery, (Walters & Karram eds.) pp. 235-256 (Mosby 1999).
Kovac, S. Robert, et al, Pubic Bone Suburethral Stabilization Sling: A Long Term Cure for Sui?, Contemporary OB/GYN, 10 pages (Feb. 1998).
LigiSure Atlas™, Tyco Healthcare, Valleylab®, 2 pages (no date).
Mitek Brochure, Therapy of Urinary Stess Incontinence in Women Using Mitek GIII Anchors, by Valenzio C. Mascio, MD.
Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advaned Surgical Techniques, vol. 9, No. 1 p.
Readjustable REMEEX® system, Neomedic International, 8 pages (no date).
SABRE™ Bioabsorbable Sling, Generation Now, Mentor, 4 pages (May 2002).
SABRE™ Surgical Procedure, Mentor, 6 pages (Aug. 2002).
Sanz, Luis E. et al., Modification of Abdominal Sacrocolpopexy Using a Suture Anchor System, the Journal of Reproductive Medicine, vol. 48, n. 7, pp. 496-500 (Jul. 2003).
Ulmsten, U. et al., An Ambulatory Surgical Procedure Under Local Anesthesia for Treatment of Female Urinary Incontinence, International Urogynecology Journal, vol. 7, pp. 81-86 (May 1996).
Ulmsten, Ulf et al., A Three Year Follow Up of Tension Free Vaginal Tape for Surgical Treatment of Female Stress Urinary Incontinence, British Journal of Obstetrics and Gynaecology, vol. 106, pp. 345-350 (1999).
UroMed Access Instrument System for the Sub-urethral Sling Procedure Catalog No. 120235, Directions for Use, (3 pages).
Vesica® Percutaneous Bladder Neck Stabilization Kit, A New Approach to Bladder Neck Suspenison, Microvasive® Boston Scientific Corporation, 4 pages (1995).

* cited by examiner

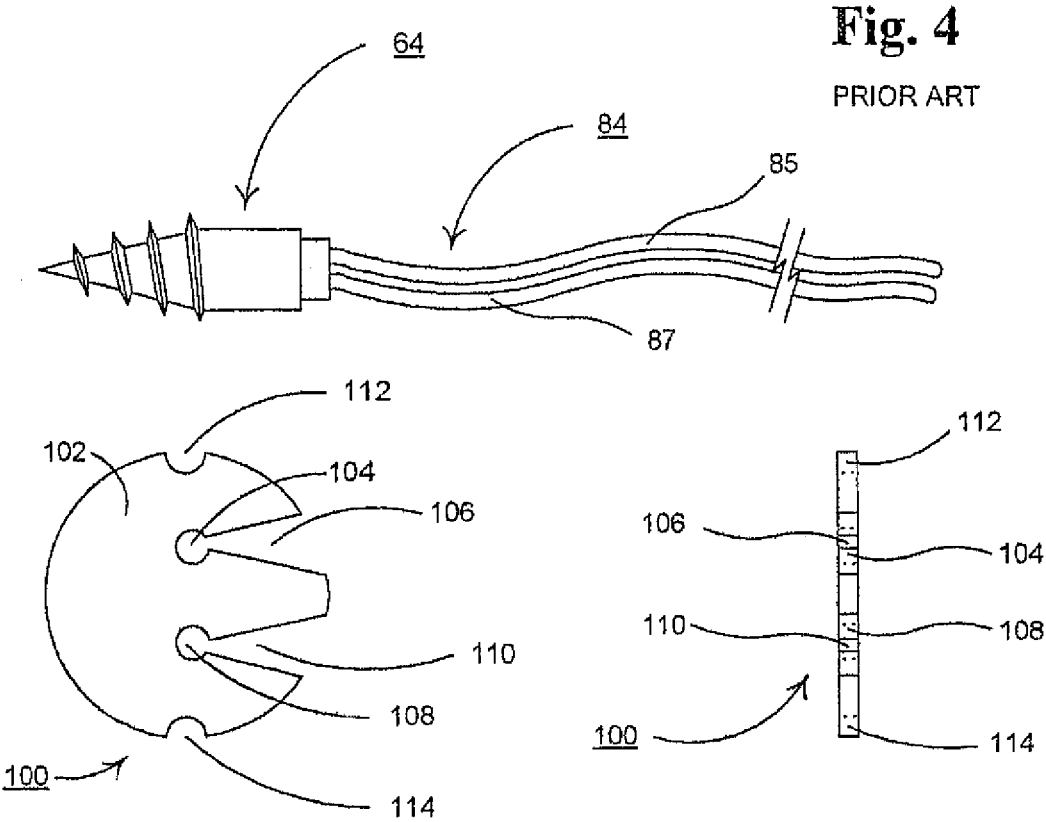
Fig. 4
PRIOR ART
Fig. 5
Fig. 6
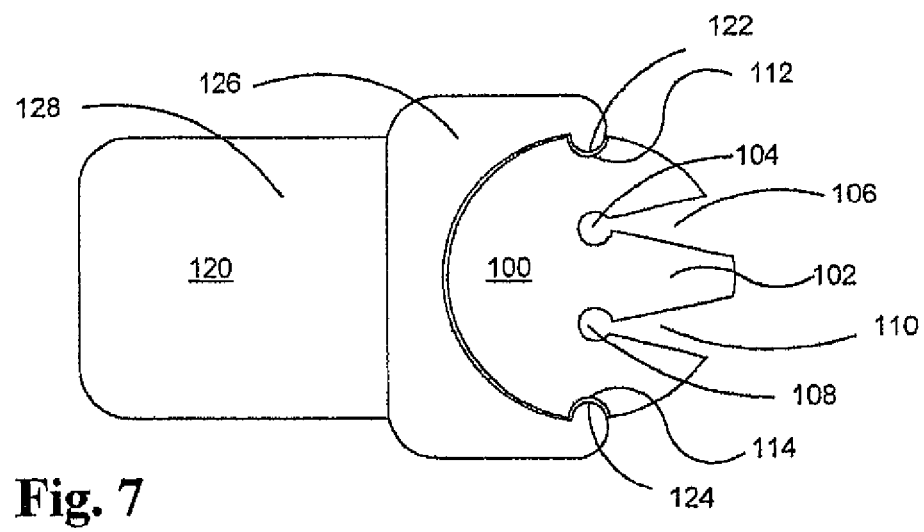
Fig. 7

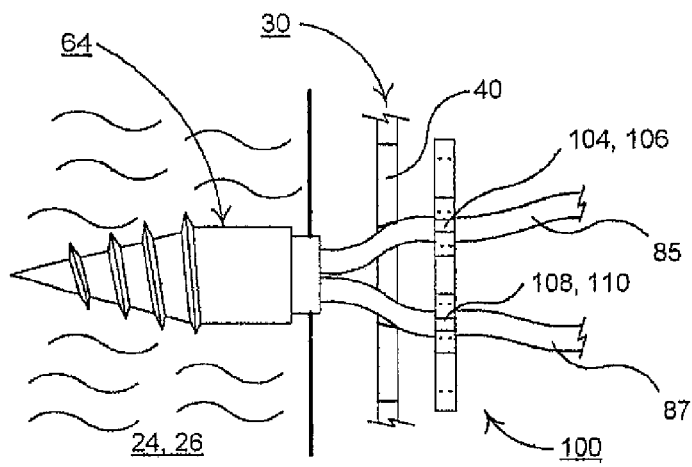
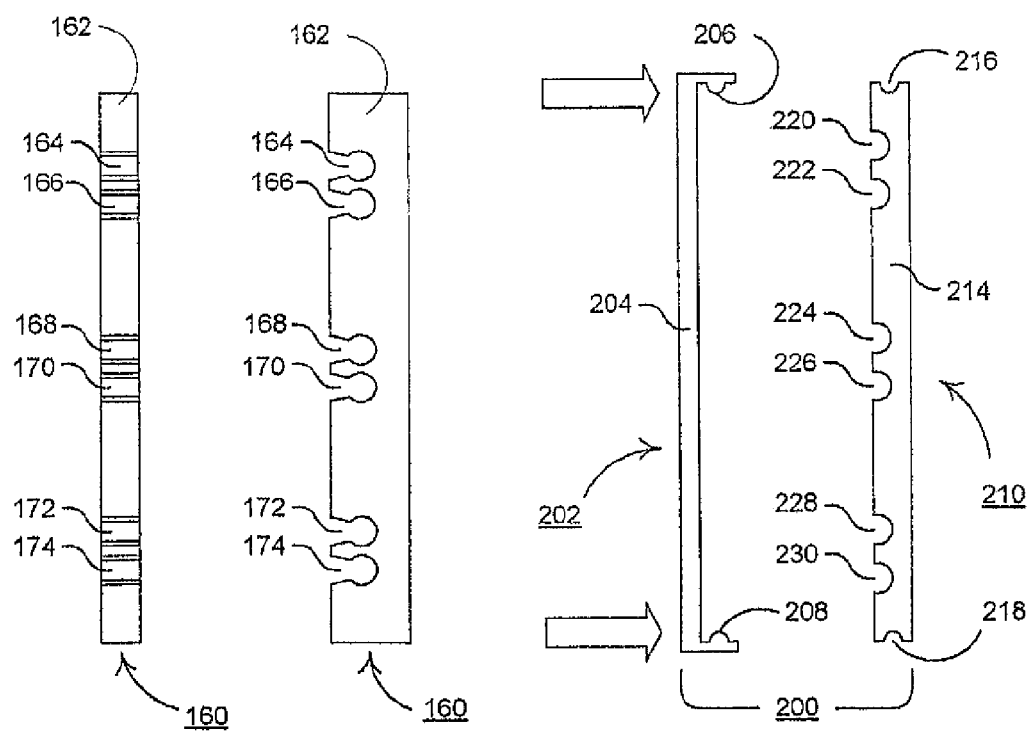
Fig. 8
Fig. 10    Fig. 11    Fig. 12

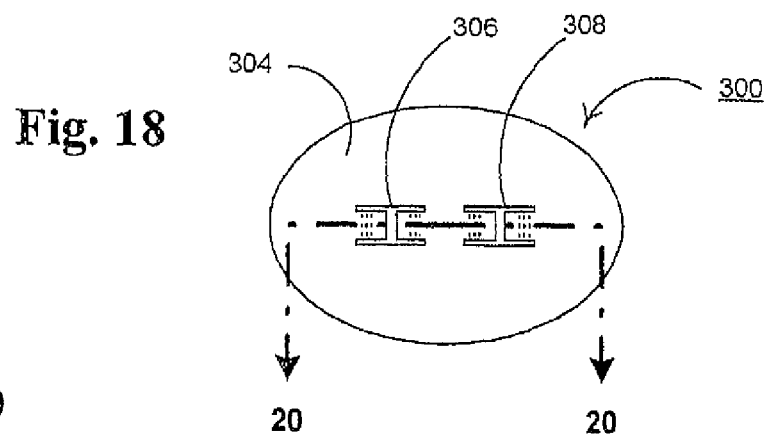
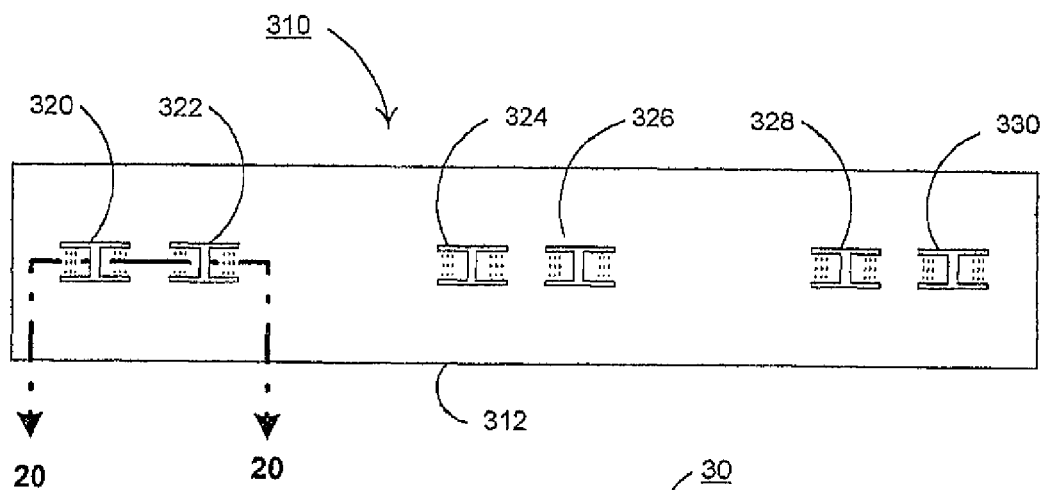
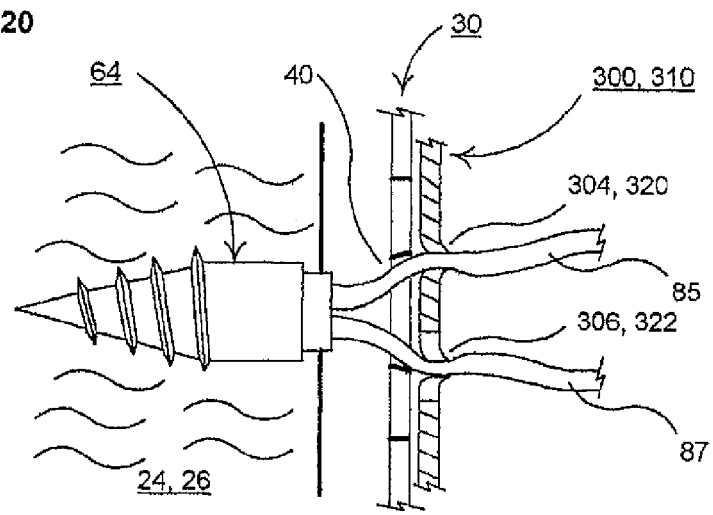

SURGICAL KIT FOR SECURING AN IMPLANTABLE SLING IN A PUBIC REGION

RELATED APPLICATIONS

This application is a continuation application of U.S. patent application Ser. No. 11/993,441, filed Dec. 9, 2009, which claims the benefit from International Application No. PCT/US2006/023956, having PCT Publication No. WO 2007/002071, which was filed on Jun. 20, 2006, which in turn claims priority under 35 USC §119(e) from U.S. Provisional Patent Application having Ser. No. 60/692,667, filed on Jun. 21, 2005, wherein these applications are incorporated herein by reference in their entireties.

BACKGROUND

Incontinence is a condition characterized by involuntary loss of urine, beyond the individual's control, that results in the loss or diminution of the ability to maintain the urethral sphincter closed as the bladder fills with urine. Male or female stress urinary incontinence (SUI) occurs when the patient is physically or emotionally stressed.

One cause for this condition is damage to the urethral sphincter or loss of support of the urethral sphincter, such as can occur in males after prostatectomy or following radiation treatment, or that can occur due to pelvic accidents and aging related deterioration of muscle and connective tissue supporting the urethra. Other causes of male incontinence include bladder instability, over-flowing incontinence and fistulas.

The female's natural support system for the urethra is a hammock-like supportive layer composed of endopelvic fascia, the anterior vaginal wall, and the arcus tendineus (a distal attachment to the pubic bone). Weakening and elongation of the pubourethral ligaments and the arcus tendineus fascia pelvis, weakening of the endopelvic fascia and pubourethral prolapse of the anterior vaginal wall, and their complex interaction with intraabdominal forces are all suspected to play a role in the loss of pelvic support for the urethra and subsequent hypermobility to an unnaturally low non-anatomic position, leading to urinary incontinence.

Females can also exhibit cystocele, a condition due to laxity of the pelvic floor wherein the bladder extrudes out and downwards causing SUI. The severity of this bladder collapse is rated between Grades one through four. In Grade four cystocele, the bladder extrudes out of the vaginal opening. The treatment of choice for this condition includes the reduction or closing of the pelvic floor opening from which the bladder descends using sutures. As noted below, other procedures involving implantation of a urethral sling are also gaining acceptance.

In general, continence is considered to be a function of urethral support and coaptation. For coaptation to successfully prevent or cure incontinence, the urethra must be supported and stabilized in its normal anatomic position.

The present application is directed to the treatment of SUI and chronic urinary incontinence due to inability of the urethral sphincter to close or remain closed as bladder fluid pressure builds. Currently, incontinence treatments of choice involve implantation of a Kaufman Prosthesis, an artificial sphincter (such as the AMS-800 Urinary Control System available from American Medical Systems, Inc.), or a urethral sling procedure in which a urethral sling is inserted beneath the urethra and advanced in the retro pubic space. Peripheral portions of the elongated urethral sling are affixed to bone or body tissue, and a central portion of the elongated urethral sling extends under the urethral or bladder neck to provide a platform that compresses the urethral sphincter, limits urethral distention, and pelvic drop, and thereby improves coaptation.

Male and female urethral sling procedures are disclosed in commonly assigned U.S. Pat. Nos. 6,652,450 and 6,382,214, for example, and further female urethral sling procedures are described in commonly assigned U.S. Pat. No. 6,641,524, for example, and publications and patents cited therein. The implantation of certain urethral slings involves the use of delivery systems configured for and techniques that involve transvaginal, transobturator, suprapubic and pre-pubic exposures or pathways.

The above-referenced '214 patent describes apparatus and methods for treatment of male incontinence and female cystocele repair in which a urethral sling material is positioned between the descending pubic rami of the pubic bone. In such an operation a "hammock-like" urethral sling material is sutured below the urethra in males, or below the posterior bladder wall in the case of cystocele in females. The urethral sling material may comprise synthetic material or cadaveric or autologous fascia and may or may not be absorbable over time.

In the male case, the urethral sling applies passive compression against the bulbar urethra. The compression, either by itself or in conjunction with urethral mobility, prevents urine leak during strain. If additional passive pressure is required on the urethra after surgery is completed, collagen or other bulky material can be injected with a tiny needle through the perineum, causing more pressure created by the bulky material on one side (the lower or caudal side) by the urethral sling, and on the other (the upper or superior) side compressing the urethra. An example of a urethral sling sutured to and extending between four bone screws fixed to the descending pubic rami is depicted in FIG. 12 of the above-referenced '214 patent.

One minimally invasive surgical procedure that incorporates the teachings of the above-referenced '214 patent to alleviate mild to moderate male SUI is performed employing the InVance™ Male Urethral Sling System for implanting the InteMesh™ Synthetic Surgical Mesh (both available from American Medical Systems, Inc.) in a manner generally described in the above-referenced '214 patent and depicted in FIGS. 1-3. The InteMesh™ Synthetic Surgical Mesh is about 4 cm×7 cm and knitted from a supple polyester material coated with silicone, the knitted mesh having a pore size that allows for tissue ingrowth during chronic implantation. The InVance™ Male Urethral sling System includes four to six, typically, titanium bone screws and a disposable, battery powered, inserter or driver. Each bone screw has a distal self-tapping spiral thread and a length of No. 1 Prolene suture extending proximally from the bone screw.

In the implantation procedure, the patient is first placed in the lithotomy position and draped, and the surgical field is prepared. A 16 French Foley catheter, for example, is inserted into the urethra, the catheter balloon is inflated t to assist the surgeon in identifying the urethra during dissection, and the scrotum is elevated. A vertical incision is made over the midline in the perineum, and the skin and subcutaneous tissues are dissected free. The bulbocavernous muscle is then exposed, and dissection is carried out posteriorly to the area of the transverse perineum to completely free the bulbar urethra. Lateral dissection is used to expose the corpora cavernosum and the descending pubic rami.

The six titanium bone screws or anchors are then screwed, one at a time, into the inner portion of the descending pubic rami of the pubic bone using the battery-powered driver. The bone screws are screwed fully into the pubic bone so that the No. 1 Prolene sutures extend outward from each bone. The location of each bone screw and the order of bone screw insertion can be selected by the surgeon. In one approach, the first pair of bone screws is inserted just below the symphysis, the second pair is inserted just proximal to the level of the ischial tuberosity, and the third pair is inserted intermediate the first and second pair.

The InteMesh™ Synthetic Surgical Mesh is then applied against the array of bone screws bridging the lower surface of the bulbar urethra between the descending pubic rami to determine where the sutures will be passed through the mesh pores and tied off. The sutures extending from one of the descending pubic rami may be first passed though selected mesh pores and tied off employing several surgeon's suture knots. Tension is then applied to the other side or end of the urethral sling as it is drawn against the other pubic ramus to determine where the bone screw sutures should be passed through the mesh pores and tied off.

The determination of the appropriate tension may be accomplished using a cough test or Retrograde Perfusion Pressure (RPP) test. To perform a RPP test, the Foley catheter balloon is then deflated, and the Foley catheter is withdrawn and connected to a sterile saline perfusion line. A zero pressure state is obtained by lowering the bag to the level of the symphysis. The tip of the catheter is repositioned at the penoscrotal angle, and the urethral resistance to start of flow or leakage is recorded (by distance of the bag above the level of the symphysis). In patients under anesthesia suffering from sphincter incontinence, the urethral resistance is very low. Tension is then applied to the untied side of the urethral sling by advancing the end of the urethral sling along the sutures toward the bone screws so that the urethral sling bears against the bulbar urethra. The mesh urethral sling compresses the bulbar urethra as it is adjusted in tension to increase urethral resistance to withstand a pressure selected between 30 and 60 cm of water. The sutures are then tied to maintain the selected tension.

The Foley catheter is then advanced to the bladder (which should advance without difficulties), and the wound is irrigated with Bethadine solution and closed in layers. Subsequently, the Foley catheter is removed after 2 hours, and the patient can be discharged home on oral antibiotics and pain medication after completing a successful voiding trial.

The above-referenced '214 and '524 patents also disclose procedures for repairing a cystocele using retropubic and lateral pubic bone anchors. The surgery disclosed in the '214 patent is indicated for patients with grade four cystocele and urethral hypermobility. The procedure repairs the central defect, the lateral defect, approximates the cardinal ligaments to the midline, and creates a urethral sling of the urethra.

After preparation and draping, a Foley catheter is inserted in the bladder. Once the catheter is in place, a "goal post" incision is made. The vertical bars of the goal post extend laterally from the distal urethra to the horizontal bar that is made just proximal to the bladder neck. The vertical bars reach the vaginal cuff.

After creation of the goal post incision, the vaginal wall is dissected free to expose the perivesical fascia laterally and the cardinal ligaments posteriorly. A figure eight 2-0 absorbable suture is applied to approximate the cardinal ligament to the midline without tying it. If an enterocele sac is encountered, it should be repaired at this stage.

The retropubic space is then entered over the periurethral fascia at the level of the vertical bars of the incision, and the urethropelvic ligaments are exposed. Two fascial anchors (the upper pair) are inserted into the tissue of the suprapubic area. Each of these anchors comprises a bone screw having a distal self-tapping screw thread of the type described above with a No. 1 Prolene suture attached to the proximal end of the bone screw.

In an alternative embodiment, at this stage of the procedure, the retropubic space is not open and two bone anchors or screws of the type described above are applied to the inner surfaces of the symphisis using a right angle drill.

After application of the first set of anchors, a second pair of bone anchors or screws of the type described above are applied to the inner surface of the descending pubic rami of the symphysis.

Once the four bone screws are in place, the bladder prolapse is reduced using a moist sponge over a right angle retractor. Alternatively, a Dexon mesh is applied and left in place. The lower pair of Prolene sutures is then used to incorporate the perivesical fascia and the cardinal ligaments area. Interrupted 2-0 absorbable sutures are used to approximate the perivesical fascia to the midline over the Dexon mesh.

A variation on this procedure is set forth in commonly assigned, U.S. Patent Application Publication No 2002/0183762 to provide urethral support and coaptation employing the InFast™ Ultra Transvaginal Urethral sling System for implanting a urethral sling selected from among the InteXen™ Porcine Dermal Matrix or the InteDerm™ Allograft Dermal Matrix or the InteLata™ Allograft Fascia Lata (all available from American Medical Systems, Inc.). The selected urethral sling is intended to be cut to size and in a T-shape to fit between the bone screws and to be attached thereto as described above. The InFast™ Ultra Female Urethral sling System includes four, typically, titanium bone screws and a disposable, battery powered, inserter that positively engages the bone screw to drive it into bone. In this system, a length of No. 1 Prolene suture is passed through a metal ring extending proximally from the bone screw, and the ends of the suture are joined to needles adapted to be passed through the urethral sling. A distal end of a drive shaft of the battery-powered inserter engages the bone screws, and the drive shaft is shaped to enable orientation of the screw threads toward the posterior aspect of the pubic bone. Other types of bone anchors that include a penetrating tip, a shaft, and a suture threaded through the shaft and that are adapted to be inserted into bone are disclosed in commonly assigned U.S. Pat. Nos. 6,635,058 and 6,746,455.

The tensioning of the selected urethral sling is accomplished in this procedure as the suture needles are passed through the urethral sling, and the urethral sling is pressed against the bone surface. The suture needles are severed, and the suture ends are tied together. The tied suture knot is slid upward and posteriorly (behind the bone) to ensure juxtaposition of the sling end to the bone surface.

The above-described bone screws are intended to be driven into the bone until completely embedded with the suture extending out of the self-tapped bore in the bone.

Thus, in the above-described procedures, the urethral sling in maintained in place, and sling tension is adjusted and applied through the tied sutures. The procedure of initially tensioning and tying the sutures takes an undue amount of the surgical time, up to 15-25 minutes as observed in some instances employing the InVance™ Male Urethral Sling System for implanting the InteMesh™ Synthetic Surgical Mesh. Moreover, it is sometimes difficult to achieve the tension in the urethral sling that is sufficient to constrict the urethral sphincter to provide urethral resistance to leakage at the selected water bag height, e.g. at 60 cm.

If the resulting sling tension is not adequate, it may be necessary to untie the tied sutures to readjust tension including possibly repositioning the bone screw in the pubic bone or the sutures extending through the urethral sling. Tying, untying and retying the suture knots consumes further time. Thus, it would be desirable to simplify the process of and to reduce the amount of time that it takes to detach, adjust tension, and reattach the urethral mesh to the sutures extending from bone screws.

Moreover, the sutures may have been trimmed at the knot following an earlier tying. Applying tension through and retying the trimmed sutures may be difficult to accomplish. Therefore, it would be desirable to simplify the process of tensioning and retying the sutures in a manner that is not compromised by trimming the suture length.

In addition, redundant knots are often tied to increase reliability of the suture knot, and the size of the knots so formed can irritate adjacent enervated tissue, causing discomfort to the patient. Consequently, it would be desirable to minimize the physical size of suture fixation of the urethral sling to the bone anchors or screws.

Various types of bone anchors that include a penetrating tip, a shaft, and a head and are adapted to be inserted into bone are disclosed in commonly assigned U.S. Pat. Nos. 6,328,744, 6,387,041, 6,544,273, 6,730,110, and 6,843,796. In certain embodiments disclosed in the '041 patent, for example, the head extends at an angle to the shaft axis, and may comprise laterally extending arms or may comprise a circular plate, a sphere or a half-sphere. In use, the tip is advanced through the sling so that the sling bears against the shaft and is maintained there by the head.

The preferred embodiments of the present invention incorporate a number of inventive features that address the above-described problems that may be combined as illustrated by the preferred embodiments or advantageously separately employed.

SUMMARY

The kits, tools, and/or components of the preferred embodiments of the present invention may be employed to affix a sling to a bone or bones, in particular, a urethral sling to pubic bones. The urethral sling may be of any type having opposed sling sides and extending between a first sling end adapted to be coupled to a first pubic bone and a second sling end adapted to be coupled to a second pubic bone to fix the urethral sling in a sub-urethral location to support the urethra and alleviate incontinence. The urethral sling may be formed of material having sling openings extending through it at least in portions adjacent the first and second sling ends. In the case that the urethral sling is formed of a mesh having mesh pores for tissue ingrowth, mesh pores may be selected to function as sling openings. Alternatively, the urethral sling may be formed of a material capable of being perforated in the surgical procedure to form sling openings extending through it at least in portions adjacent the first and second sling ends.

The kits, tools and/or components of the preferred embodiments of the present invention include bone anchors adapted to be attached to bone, e.g., pubic bone, with elongated sutures extending from the bone anchor bodies. The sutures extending proximally from the anchor bodies are adapted to be threaded through sling openings in any of the manners described above. Suture retainers are adapted to engage the sutures to apply retentive forces against the urethral sling to retain portions of the urethral sling proximate the pubic bones. Sling tension testing may proceed and repositioning may occur until satisfactory sling tension is achieved.

In one aspect of the present invention, the retainers comprise retainer bodies having at least one retainer bore therethrough sized to receive and frictionally engage one or more suture to inhibit slippage of the suture(s) with respect to the retainer bore, whereby a surface of the suture retainers is adapted to be applied against portions of the urethral sling to retain the sling portions proximate the pubic bones. The suture retainers have surface areas adapted to bear against the sling that exceed the cross-section areas of the sling openings.

The bone anchors that are attached to the pubic bones may comprise one or more suture extending to a suture free end, the suture(s) adapted to be extended through sling openings so that portions of the sling are applied proximate the pubic bones. Certain embodiments of suture retainers are adapted to be applied to each suture(s) extending through the sling openings of the urethral sling. Other embodiments of suture retainers are adapted to be applied to a plurality of suture(s) extending from a plurality of bone anchors through a plurality of sling openings of the urethral sling.

In certain embodiments, the suture(s) extending from each bone anchor has a substantially constant cross-section area through substantially the entire length of the suture. In alternative embodiments, the suture(s) extending from each bone anchor is configured to positively engage the urethral sling and/or a suture retainer. The retainer bore cross-section area is selected to be somewhat smaller than the suture cross-section area where the suture extends through the retainer bore, whereby the retainer bore frictionally engages the suture with an engagement force that inhibits slippage along the suture.

In exemplary preferred embodiments, the suture retainer body is shaped having a laterally extending slot extending to or providing the retainer bore. In use, each bone anchor suture is extended through a laterally extending slot into a retainer bore of the suture retainer. The retainer may be advanced along the suture into engagement with a portion of the urethral sling (if necessary) by applying sufficient force to overcome the frictional engagement force.

In other exemplary preferred embodiments, a slot is not provided to enable lateral insertion of the suture into the retainer bore. Each suture is inserted through a retainer bore, and the suture retainer is advanced along the suture(s) into engagement with a portion of the urethral sling by applying sufficient force to overcome the frictional engagement force. The suture retainer may be resilient, having retainer bore(s) sized and shaped to be expanded when advanced over the suture as the suture retainer is advanced toward the bone anchor and to resist retraction over the suture away from the bone anchor.

In further exemplary preferred embodiments, the bone anchor suture is not uniform in cross-section area along its length. The suture is shaped along at least a portion of the suture length with at least one suture fixation element that extends outward to abut or engage the suture retainer to maintain it against the urethral sling and inhibit slippage. In use, the suture body between fixation elements may be inserted laterally through a slot and into a retainer bore of a suture retainer, whereby the suture retainer is disposed between the sling and the fixation element.

In another preferred embodiment, the suture retainer and fixation element(s) are complementary in shape so that the suture retainer may be applied over the free end of the bone anchor suture(s) and advanced toward the urethral sling over one or a plurality of suture fixation elements. The suture retainer is applied against a portion of the urethral sling and maintained in position by a suture fixation element abutting the suture retainer. For example, the suture retainer may be resilient and have a retainer bore sized and shaped to be expanded when advanced over the outwardly extending fixation elements as the suture retainer is advanced toward the bone anchor. The contraction of the retainer bore engages the suture to inhibit retraction of the suture retainer over the suture away from the bone anchor.

In a still further aspect of the present invention, a tool is employed to apply the suture retainer to the suture(s) to press and entrap the urethral sling material against the pubic bone.

Advantageously, procedures for attaching the urethral sling to bone anchors or anchors are simplified to shorten the surgical time, the tensioning and fixation are made more reliable, and the resulting suture knots are reduced in size or eliminated.

In use for retaining a urethral sling against body tissue proximate the urethra, a first plurality of bone anchors are affixed to a first pubic bone and a second plurality of bone anchors are affixed to a second pubic bone. The bone anchor sutures of the first plurality of bone anchors are passed through the sling openings along a first end of the urethral sling. A suture retainer having a plurality of retainer bores or a plurality of suture retainers are applied to the sutures of the first plurality of bone anchors to engage and retain the first end of the urethral sling proximate the first pubic bone. The urethral sling is tensioned as the second plurality bone anchor sutures are drawn through sling openings along the second end of the sling. A suture retainer having a plurality of retainer bores or a plurality of suture retainers are applied to the sutures of the second plurality of bone anchors to engage and retain the second end of the urethral sling proximate the second pubic bone. The urethral sling is thereby entrapped engaged and tensioned between the pubic bones and the suture retainers. The suture retainers may be released so that the urethral sling may be quickly detached and reattached to change sling tension as tension testing dictates.

Advantageously, the end portions of the sutures proximate the suture retainers may be trimmed or tied off and trimmed after adequate tension is achieved and with fewer knots to reduce suturing time and the final exposed suture bulk.

Bone anchors usable in the practice of the present invention may comprise bone screws having spiral thread bone fixation mechanisms adapted to be screwed into bone or tapered, pointed, bone tack bone fixation mechanisms adapted to be advanced into bone, as disclosed for example in the above-referenced, commonly assigned '058, '273 and '041 patents, or any other form of bone fixation mechanism.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 4 is an expanded side view of a bone anchor, particularly a bone screw of the type employed in FIGS. 1 and 2, with a pair of bone screw sutures extending from the screw head;

FIG. 5 is a top view of a first embodiment of a suture retainer employable with the suture pair of the bone screw of FIG. 4;

FIG. 6 is a side view of the suture retainer of FIG. 5;

FIG. 7 is a top view of a dispenser coupled to the suture retainer of FIGS. 5 and 6 to be employed in the fixation of the retainer to the sutures of the bone screw of FIG. 4;

FIG. 8 is a plan view in partial section of the bone screw of FIG. 4 screwed into pubic bone and the suture retainer of FIGS. 5-7 engaging the sutures and retaining the mesh of the urethral sling of FIG. 3 proximate the pubic bone;

FIG. 10 is a side view of a further embodiment of a suture retainer employable with a plurality of suture pairs extending from a plurality of bone screws of FIG. 4;

FIG. 11 is a top view of the suture retainer of FIG. 10;

FIG. 12 is a top view of a still further embodiment of a suture retainer employable with a plurality of suture pairs extending from a plurality of bone screws of FIG. 4;

FIG. 18 is a top view of a further embodiment of a suture retainer employable with the suture pair of the bone screw of FIG. 4;

FIG. 19 is a top view of a further embodiment of a suture retainer employable with the suture pair of a plurality of the bone screws of FIG. 4;

FIG. 20 is a plan view in partial section of the bone screw of FIG. 4 screwed into pubic bone and the suture retainer of FIG. 18 or FIG. 19 engaging the sutures and retaining the mesh of the urethral sling of FIG. 3 proximate the pubic bone;

Figure 1:
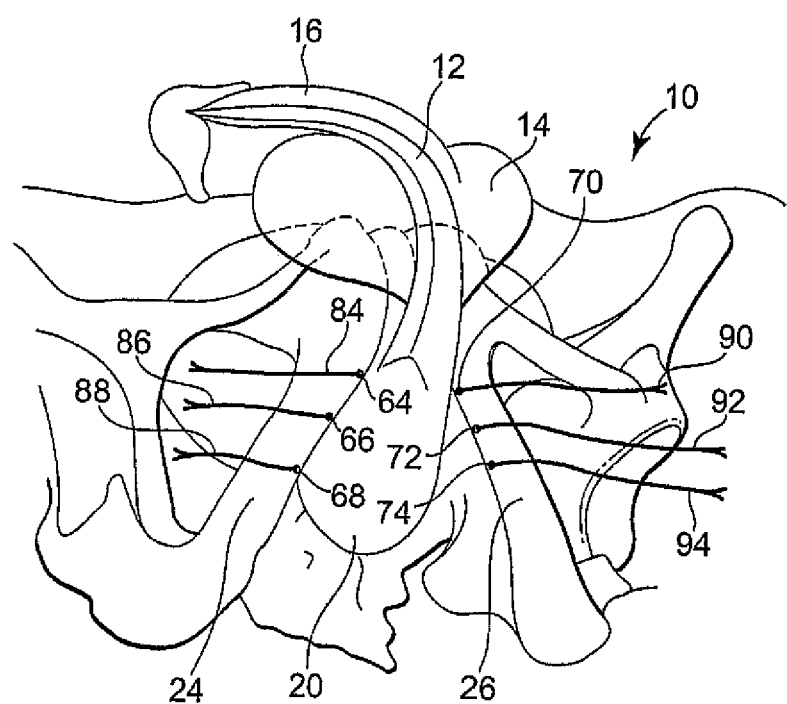
FIG. 1 is a schematic illustration of the fixation of bone anchors, e.g., bone screws, to descending pubic rami with sutures extending from the bone screws in accordance with the prior art.

It will be understood that the drawing figures are not necessarily to scale.

DETAILED DESCRIPTION

In the following detailed description, references are made to illustrative embodiments of methods and apparatus for carrying out the invention. It is understood that other embodiments can be utilized without departing from the scope of the invention. Preferred methods and apparatus are described for affixing urethral slings fixed to pubic bones, particularly the descending pubic rami.

It will be understood that the term "urethral sling" encompasses any type of sling, tape, hammock or the like that supports and or/applies compression to the urethra. One exemplary form of urethral sling is illustrated in the figures and described below in use of the kits, tools, and/or components of the preferred embodiments of the present invention that is formed of a mesh having mesh pores that facilitate tissue ingrowth. As noted above, the urethral sling may be formed of any biocompatible flexible sheet material known in the art with or without pores or sling openings through the sheet material.

Furthermore, while the bone anchor embodiments are illustrated and described having an anchor body bearing a bone fixation mechanism comprising a spiral thread adapted to be screwed into bone, it will be understood that the principles of the present invention are applicable to other forms of bone anchors.

Figure 2:
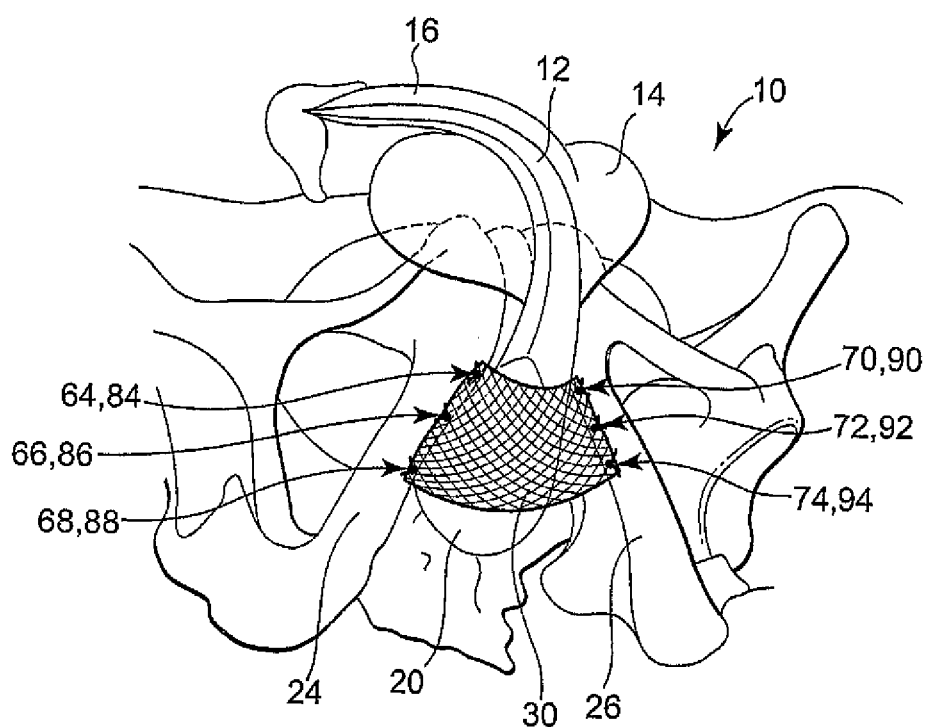
FIG. 2 is a schematic illustration of the fixation of a urethral sling to the bone screws of FIG. 1 with the sutures extending from the bone screws in accordance with the prior art.

Referring to FIGS. 1 and 2, the male anatomy in the pelvic region 10 is depicted schematically to illustrate how a urethral sling 30 is affixed to the right and left descending pubic rami 24 and 26 to extend across and support the male urethra 12 in the manner described above, for example, in the procedure employing the InVance™ Male Urethral Sling System for implanting the InteMesh™ Synthetic Surgical Mesh urethral sling.

Figure 3:
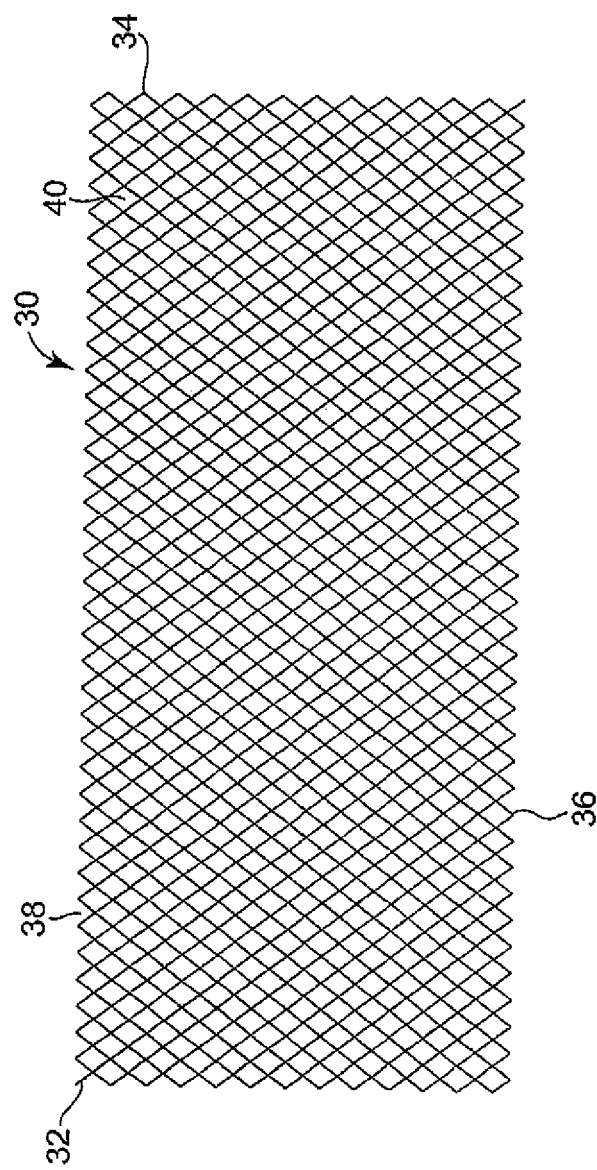
FIG. 3 is an enlarged plan view of a prior art urethral sling formed of a mesh and adapted to be attached to the descending pubic rami as shown in FIG. 2.

An embodiment of the urethral sling 30, which can correspond to the InteMesh™ Synthetic Surgical Mesh urethral sling, is depicted in greater detail in FIG. 3. In a preferred embodiment, the urethral sling 30 is knitted into a mesh from a supple polyester yarn to have a plurality of sling openings comprising mesh pores 40 bounded by yarn strands and may be coated with medical grade silicone rubber. The knitted mesh pores 40 have a pore size that allows for tissue ingrowth therethrough during chronic implantation. The urethral sling 30 extends end-to-end between first and second sling ends 32 and 34 and side-to-side between first and second sling sides 36 and 38.

Returning to FIGS. 1 and 2, as noted above, the surgical field is prepared after the patient, placed in the dorsal lithotomy position and draped. The scrotum 14 and penis 16 are elevated, a vertical incision is made over the midline in the perineum of the skin and subcutaneous tissues (not shown) are dissected to the side to expose the bulbocavernous muscle 20. Lateral dissection is used to expose the corpora cavernosum 22 and the surfaces of the descending pubic rami 24 and 26.

As shown in FIG. 1, the illustrated fixation of the surgical urethral sling 30 is effected employing six titanium bone screws 64, 66, 68, 70, 72, 74 sequentially driven by a disposable, battery powered, inserter or driver (not shown). Each bone screw 64, 66, 68, 70, 72, 74 has a distal self-tapping spiral thread adapted to be screwed into bone when the screw tip is applied to the bone surface and the driver is powered. A pair of No. 1 Prolene sutures 84, 86, 88, 90, 92, 94 extend proximally from each bone screw 64, 66, 68, 70, 72, 74, respectively. One such bone screw 64 with the pair of bone screw sutures 84 extending from the screw head is depicted in the expanded view of FIG. 4. Typically, the pair of bone screw sutures is crimped at one end into a bore of the bone screw and extends about 30 cm to bone screw suture free ends. The bone screw suture free ends can be joined as by use of ultrasonic welding to ease in handling and use of a bone screw fixation tool. The surgeon may choose to pass the joined suture free ends through a selected mesh pore, tie a knot or knots, and then trim the sutures. Or, the surgeon may first trim the sutures, separately pass the severed suture free ends through a common or separate mesh pores, tie a knot or series of knots, and again trim the suture free ends.

The bone screws 64, 66, 68, 70, 72, 74 are screwed fully into the bone so that the No. 1 Prolene sutures 84, 86, 88, 90, 92, 94, respectively, extend outward of the descending pubic rami 24 and 26 as shown in FIG. 1. The surgeon can select the location of each bone screw 64, 66, 68, 70, 72, 74 and the order of insertion. In one approach depicted in FIG. 1, a first pair of bone screws 64, 70 is inserted just below the symphysis, the second pair 66, 72 is inserted proximal to the level of the ischial tuberosity, and the third pair 68, 76 is inserted intermediate the first and second pair.

The urethral sling 30 is then applied against the array of bone screws 64, 66, 68, 70, 72, 74 bridging the lower surface of the bulbar urethra 20 between the descending pubic rami 24 and 26 to determine where each suture of the respective suture pairs 84, 86, 88, 90, 92, 94 will be passed through mesh pores.

The free ends of each suture of each suture pair 84, 86, 88, 90, 92, 94 are sequentially grasped, passed through separate mesh pores and drawn tight and tied together against the mesh of the urethral sling 30.

The sutures of the suture pairs 84, 86, 88 extending from the descending pubic ramus 24 may be first passed though selected mesh pores adjacent the first sling end 32. The first sling free end 32 is then pressed against the descending pubic ramus 24. The free ends of each suture of each suture pair 84, 86, 88 are sequentially grasped, drawn tight and tied together at least two times forming several surgeon's suture knots against the mesh of the urethral sling 30 firmly holding the sling first end against the descending pubic ramus 24.

Tension is then applied to the second sling end 34 of the urethral sling 30 as it is drawn against the second pubic ramus 26 to determine where the sutures of the bone screw suture pairs 90, 92, 94 should be passed through mesh pores and tied off in the manner described above. Testing for urethral resistance to leakage may be conducted employing the techniques and instruments described above as the sutures of bone suture pairs 90, 92, 94 are drawn tight against the fabric of urethral sling 30 and tied off. The sutures of bone suture pairs 90, 92, 94 may be retracted from the initially selected pores 40 and reinserted in other pores 40 in the process of optimizing the tension. In this way, the urethral sling 30 is eventually sutured to all of the bone anchors or screws 64, 66, 68, 70, 72, 74 inserted into the descending pubic rami 24 and 26 to extend laterally across and support the bulbar urethra 20. An intermediate portion of the urethral sling 30 extends between the bone screws 64, 66, 68 and the bone screws 70, 72, and 74.

The knots made with the suture pairs 84, 86, 88, 90, 92, 94 are relatively bulky and can cause irritation of tissues. In accordance with the present invention, the procedure for securing the urethral sling 30 to the descending pubic rami and tensioning the urethral sling 30 is simplified, the fastening elements are less bulky than the prevailing use of suture knots, and suture knots are eliminated in some embodiments.

The present invention may be practiced employing a variety of bone anchors. The illustrated form of bone anchor is a self-tapping bone screw that can be manually screwed into bone with a screwdriver or screwed into bone with a motor driven, battery powered screwdriver of the type described above. In each embodiment, the bone screw head or body is configured to mate with a screwdriver tip to be rotated and screwed into a pubic bone, typically the descending pubic ramus.

For convenience, the following embodiments are described in the context of attaching the urethral sling 30 of the type depicted in FIGS. 2 and 3 formed of a mesh with mesh pores 40 as described above to the descending pubic rami 24, 26 generally in at least certain of the locations of the bone screws 64, 66, 68, 70, 72, 74 or in additional locations. However, the described embodiments and techniques and their equivalents may be employed to advantageously attach any suitable urethral sling not having mesh pores but having other pre-formed sling openings extending through it or that can be perforated to make sling openings during surgery to the descending pubic rami 24, 26 or other pubic bone.

In one embodiment of the present invention depicted in FIGS. 5-9, a disk-shaped suture retainer 100 is provided for each of the bone screws 64, 66, 68, 70, 72, 74 or a lesser or greater number of bone screws screwed into the descending pubic rami 24, 26. The bone screw 64 is depicted, for example, in FIGS. 4 and 8 having the bone screw suture pair 84 comprising sutures 85 and 87 extending therefrom. The cross-section area along the length of the sutures 85 and 87 is substantially uniform.

The retainer 100 has a substantially planar retainer body 102 with retainer bores 104 and 108 extending through the retainer body 102. The retainer bores 104 and 108 are sized to receive and frictionally engage the sutures 85 and 87 to inhibit slippage of the sutures 85 and 87 with respect to the respective retainer bores 104 and 108. The retainer bores 104 and 108 have bore cross-section areas related to and somewhat smaller than the suture cross-section areas to enable frictional engagement of the sutures received within the retainer bores 104 and 108. Retainer notches or slots 106 and 110 extend from the retainer bores 104 and 108, respectively, to the circumference or edge of the retainer body 102.

The suture retainer 100 is adapted to be applied against a portion of the urethral sling 30 to retain the sling portion proximate the pubic bones. The suture retainer 100 has a major surface area adapted to bear against the urethral sling 30 that exceeds the cross-section area of the sling opening, e.g., the mesh pore 40. Thus, the suture retainer 100 is too large to be drawn through the mesh pore 40.

The suture retainer 100 is applied to extend across or laterally with respect to the sutures 85 and 87 such that the sutures 85 and 87 are first received in the respective retainer notches or slots 106 and 110 and then are compressed in cross-section area when inserted into the respective retainer bores 104 and 108, whereby the retainer bores 104 and 108 frictionally engage the sutures 85 and 87 with an engagement force that inhibits slippage along the sutures 85 and 87. The suture and retainer bore cross-section areas may be selected to enable axial advancement of the suture retainer 100 along the sutures 85 and 87 and into engagement with a portion of the urethral sling if necessary in tensioning the sling 30.

The lateral application of the suture retainer may be facilitated employing a retainer installation and dispensing tool 120 depicted in FIG. 7. The dispensing tool 120 may be about the same thickness as the suture retainer 100 and includes a substantially C-shaped clamp 126 terminating in clamp jaws 122 and 124 shaped to fit in a tool engaging feature of the retainer body 102, e.g., a pair of recesses 112 and 114 in the edge of the retainer body 102. A tab 128 extends from the C-shaped clamp 126 that is to be grasped by the surgeon between finger and thumb to position the suture retainer notches 106 and 108 with respect to the respective sutures 85 and 87 as shown in FIG. 8. The tab 128 is advanced laterally to insert the sutures 85 and 87 in the retainer bores 104 and 108, respectively. The tab 128 may then be twisted to release the clamp jaws 122 and 124 from the recesses 112 and 114 of the suture retainer 100.

Figure 9:
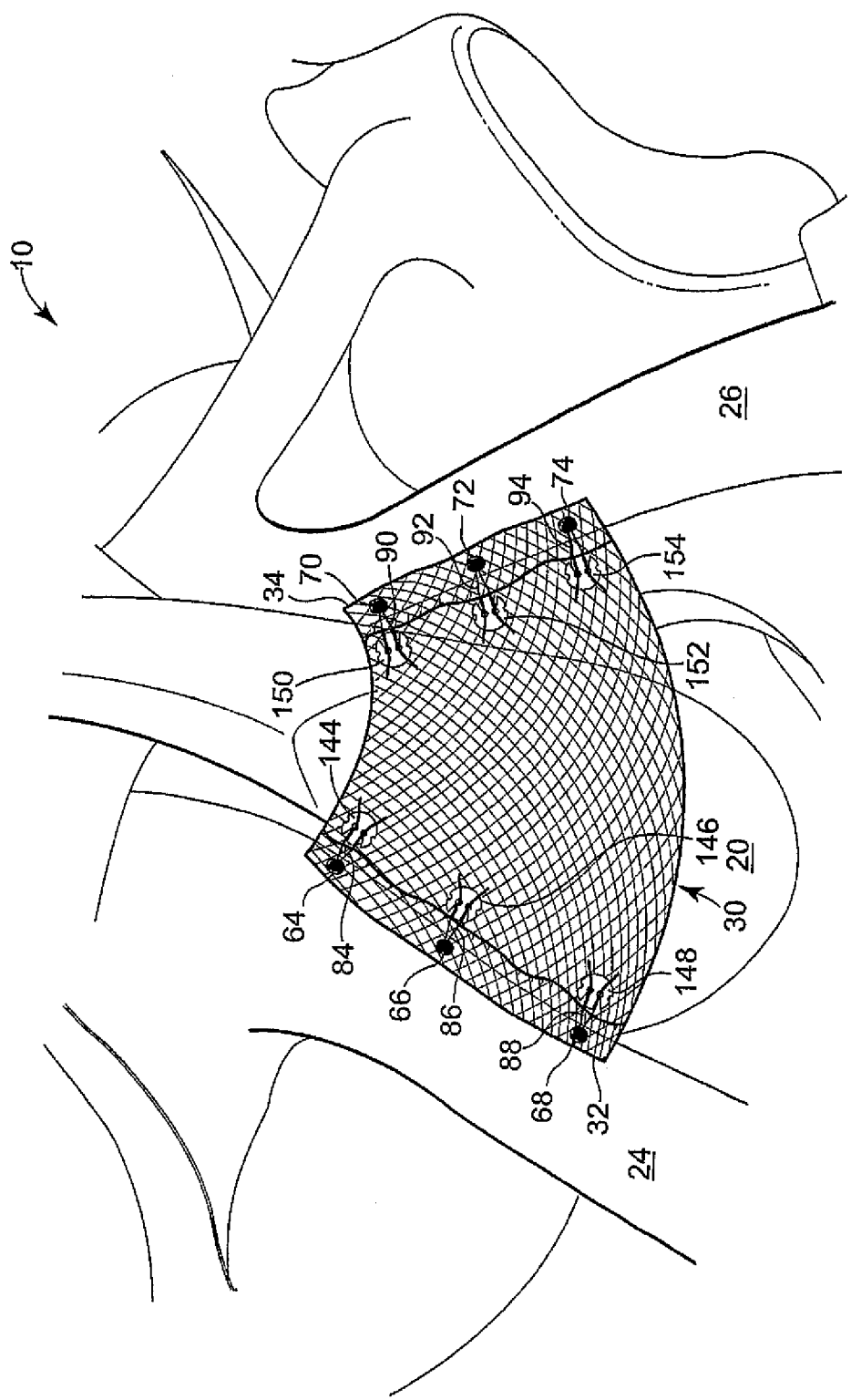
FIG. 9 is a schematic illustration of the fixation of a urethral sling of FIG. 3 with a plurality of bone screws of FIG. 4 screwed into the right and left descending pubic rami and a like plurality of suture retainer of FIGS. 5-7 engaging the sutures and retaining the mesh of the urethral sling proximate the pubic bone.

Turning to FIG. 9, the application of six such suture retainers 100, designated 144, 146, 148, 150, 152 and 154, into engagement with portions of the urethral sling 30 and with the suture pairs 84, 86, 88, 90, 92, and 94 of respective bone screws 64, 66, 68, 70, 72, and 74 is depicted. The suture retainers 144, 146, 148, 150, 152 and 154 are depicted displaced from the respective bone screws 64, 66, 68, 70, 72, and 74 for convenience of illustration. It will be understood that, in practice, the suture retainers 144, 146, 148, 150, 152 and 154 may substantially overlie and obscure the respective bone screws 64, 66, 68, 70, 72, and 74.

Thus, in use and referring to FIG. 9, the bone screws 64, 66, and 68 may be screwed into the pubic bone of the descending pubic ramus 24, and the bone screws 70, 72, and 74 may be screwed into the pubic bone of the descending pubic ramus 26. An end portion of the urethral sling 30 along sling end 32 is applied against or proximate the descending pubic ramus 24, as the suture pairs 84, 86, 88 are inserted through selected sling openings, e.g., mesh pores 40 depicted in FIG. 3. A first set of three suture retainers 100 are applied as shown in FIG. 8 to the suture pairs 84, 86, and 88 to retain the urethral sling 30 proximate the descending pubic ramus 24.

The other sling end 34 of the urethral sling 30 is then drawn across the urethra toward the descending pubic ramus 26, and the suture pairs 90, 92, 94 are inserted through selected sling openings, e.g., mesh pores 40 depicted in FIG. 3, in an end portion of the urethral sling 30 along sling end 34. A second set of three suture retainers 100 are applied as shown in FIG. 8 to the suture pairs 90, 92, and 94 to retain the urethral sling 30 proximate the descending pubic ramus 26 and to thereby tension the portion of the urethral sling 30 extending across the urethral region.

An RPP test may be conducted, and one or more of the suture retainers 144, 146, 148, 150, 152 and 154 may be adjusted along the length of the respective suture pairs 84, 86, 88, 90, 92, and 94 to adjust the sling tension if the test results are not satisfactory. The above-described steps may be repeated until the RPP test results are satisfactory. Finally, the free ends of the suture pairs 84, 86, 88, 90, 92, and 94 may be trimmed and left untied or first tied with a simple small size knot and then trimmed at the discretion of the surgeon.

Other embodiments of "multiple suture" retainers are adapted to be applied to a plurality of suture(s) extending through a plurality of openings of the urethral sling 30. Thus, first and second suture retainers may be provided that are adapted to be applied to the suture pairs 84, 86, and 88 and to the suture pairs 90, 92 and 94, respectively, or to any number of suture pairs extending from bone anchors inserted into the descending pubic rami 24 and 26.

A first embodiment of an exemplary "multiple suture" retainer 160 is depicted in FIGS. 10 and 11 that may constitute or resemble a plurality of the suture retainers 100 joined together in an elongated array. One such suture retainer 160 would be applied along the urethral sling end 32 to engage the suture pairs 84, 86 and 88, and a further suture retainer 160 would be applied along the urethral sling end 34 to engage the suture pairs 90, 92, 94.

Thus, each elongated suture retainer body 162 is generally rectangular having a major surface adapted to be pressed against a portion of the urethral sling 30 adjacent the urethral sling end 32 or 34. A series of retainer slots and bores 164, 166, 168, 170, 172, and 174 are formed extending from one side of and through the suture retainer body 162.

In use, each pair of retainer slots and bores receives and engages a respective pair of bone screw sutures. Again, the bores are sized to receive and frictionally engage the sutures passed laterally through the slots. It will be understood that the series of slots and bores 164, 166, 168, 170, 172, and 174 are schematically illustrated and may take any suitable form. It will also be understood that a greater number of slots and bores than the depicted slots and bores 164, 166, 168, 170, 172, and 174 may be formed in suture retainer body 162 arrayed along substantially the entire length of the suture retainer body 162. In such an embodiment, the surgeon may select the most suitably spaced apart slot and bore pairs to receive each suture pair.

The suture retainer body 162 is formed of a biocompatible plastic material that may be thin enough to be trimmed with shears by the surgeon to an overall size and shape accommodating the particular patient. For example, only two bone anchors or screws may be required to be placed in each pubic bone in certain instances, and the surgeon may trim the suture retainer body 162 to an appropriate size and shape leaving only two pair of the depicted slots and bores 164, 166, 168, 170, 172, and 174 to accommodate two pair of sutures.

Figure 13:
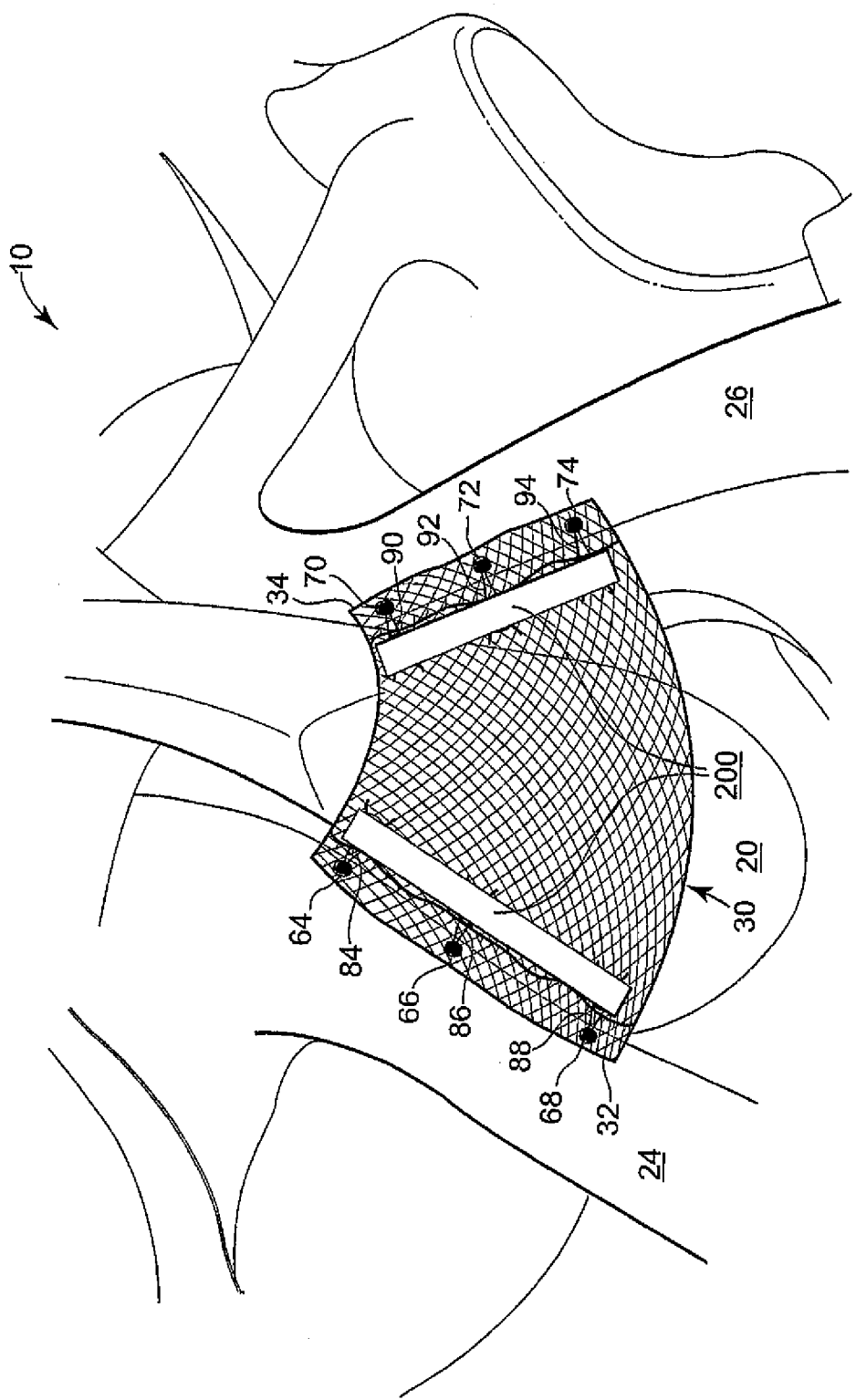
FIG. 13 is a schematic illustration of the fixation of a urethral sling of FIG. 3 with a plurality of bone screws of FIG. 4 screwed into the right and left descending pubic rami and suture retainers of FIG. 12 engaging the sutures and retaining the mesh of the urethral sling proximate the pubic bone.
Figure 14:
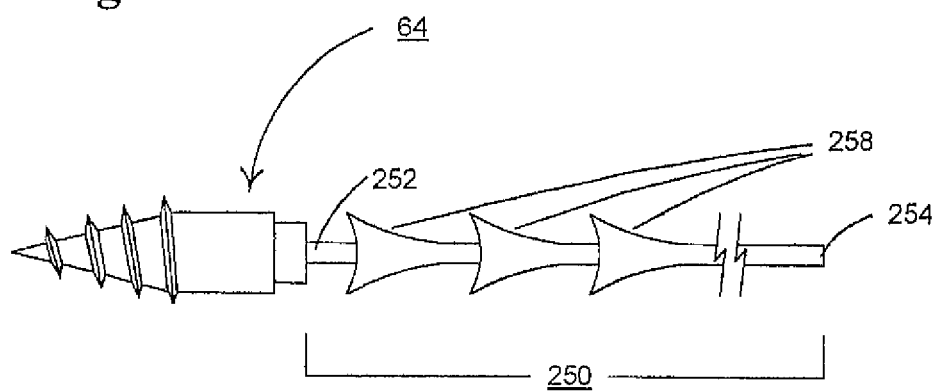
FIG. 14 is an expanded side view of a bone anchor, particularly a bone screw, with a bone screw suture extending from the screw head shaped with periodic conical or barbed fixation elements.

A further embodiment of a multiple suture retainer 200 is depicted in FIGS. 12 and 13. The multiple suture retainer 200 is formed of a retainer cover 202 and a retainer base 210 that are fitted together to entrap a number of sutures or suture pairs within suture slots and/or bores when the retainer cover 202 is fitted to the retainer base 210. The retainer cover 202 may be separate from the retainer base, as depicted in FIG. 12, or attached, e.g., by a living hinge, joining mutual ends or sides, for example. In either case, the retainer cover 202 is to be applied into engagement with or moved from an open to a closed position with the retainer base 210 to entrap and hold sutures placed through the suture slots and/or bores, and the suture retainer 200 formed of the retainer cover 202 and base 210 bears against a portion of the urethral sling 30 to hold it in place in proximity to a pubic bone.

A pair of snap recesses 216 and 218 are formed in the opposite ends, for example, of the retainer body 214. The cover body 204 is shaped and dimensioned to fit over and against the retainer body 214. A pair of snap-in catches 206 and 208 are formed in the ends of the cover body 204 that are adapted to be received in the respective snap-in recesses 216 and 218 in the ends of the retainer body 214.

In the particular illustrated embodiment of multiple suture retainer 200, a series of slots and/or suture engaging bores 220, 222, 224, 226, 228, and 230 extend into and across one major surface of the substantially rectangular retainer body 214 of the retainer base 210. Each pair of suture engaging bores 220, 222, 224, 226, 228, and 230 would receive a respective pair of bone screw sutures. Again, the bores are sized to receive and frictionally engage the sutures passed laterally through the slots. It will be understood that the series of suture engaging bores 220, 222, 224, 226, 228, and 230 are schematically illustrated and may take any suitable form. It will also be understood that a greater number of suture engaging bores than the depicted suture engaging bores 220, 222, 224, 226, 228, and 230 may be formed in suture retainer body 210 arrayed along substantially the entire length of the suture retainer body 210. In such an embodiment, the surgeon may select the most suitably spaced apart slot and/or bore pairs to receive each suture pair.

Thus, in use and referring to FIG. 13, the bone screws 64, 66, and 68 may be screwed into the pubic bone of the descending pubic ramus 24, and the bone screws 70, 72, and 74 may be screwed into the pubic bone of the descending pubic ramus 26. An end portion of the urethral sling 30 along sling end 32 is applied against or proximate the descending pubic ramus 24, as the suture pairs 84, 86, 88 are inserted through selected sling openings, e.g., mesh pores 40 depicted in FIG. 3. The suture retainer base 210 of a first suture retainer 200 is applied against the urethral sling 30 along the edge 32 and aligned with the suture pairs 84, 86, 88 to dispose the suture pair 84 in slots and/or suture engaging bores 220 and 222, the suture pair 86 in slots and/or suture engaging bores 224 and 226, and the suture pair 88 in slots and/or suture engaging bores 228, and 230. The retainer cover 202 is closed against or snapped onto the retainer base 210 to capture the suture pairs 84, 86 and 88.

The other sling end 34 of the urethral sling 30 is then drawn across the urethra toward the descending pubic ramus 26, and the suture pairs 90, 92, 94 are inserted through selected sling openings, e.g., mesh pores 40 depicted in FIG. 3 in an end portion of the urethral sling 30 along sling end 34. The suture retainer base 210 of a second suture retainer 200 is applied against the urethral sling 30 along the edge 34 and aligned with the suture pairs 90, 92, 94 to dispose the suture pair 90 in slots and/or suture engaging bores 220 and 222, the suture pair 92 in slots and/or suture engaging bores 224 and 226, and the suture pair 94 in slots and/or suture engaging bores 228, and 230. Tension may be applied to the free ends of the suture pairs 90, 92 and 94 to draw the retainer base 210 against the portion of the urethral sling 30 and thereby tension the portion of the urethral sling 30 extending across the urethral region. The retainer cover 202 is closed against or snapped onto the retainer base 210 to capture the suture pairs 90, 92 and 94.

An RPP test may be conducted, and the retainer cover 202 of either or both the first and second "multiple suture" retainers 200 removed to adjust the suture pairs and closed to entrap the suture pairs if the test results are not satisfactory. The above-described steps may be repeated until the RPP test results are satisfactory. Then, the free ends of the suture pairs 84, 86, 88, 90, 92, and 94 may be tied and/or trimmed as the surgeon prefers.

A substantially similar process is employed to dispose first and second multiple suture retainers 160 into engagement with the suture pairs 84, 86, 88 and 90, 92, 94 and against portions of the urethral sling 30 adjacent sling ends 32 and 34 to tension and hold the portions of the urethral sling 30 proximate the descending pubic rami 24 and 26.

It will be understood that the above-described suture retainers 100, 160, 200 may be employed with bone anchors, e.g., bone screws, having only one suture extending from the bone anchor by simply placing the suture through a selected suture slot and/or bore of suture retainers 100, 160, 200 or providing a single or fewer slots and/or suture engaging bores in similar suture retainers.

Moreover, it will be understood that the single suture or the sutures of a suture pair extending from a bone anchor may be especially configured to enhance frictional engagement with the urethral sling and/or the suture retainer. In such further exemplary preferred embodiments, the bone screw suture is shaped along at least a portion of the suture length between the suture free end and the suture attached end with at least one suture fixation element that extends outward to engage the urethral sling or a suture retainer interposed between the urethral sling and the suture fixation elements to maintain fixation and inhibit slippage. The suture fixation elements may take any suitable form and one suture fixation element may be provided at a suitable distance from the suture attached end or a plurality of such suture elements may be disposed at suitable intervals along the length of the suture.

In one preferred embodiment depicted in FIGS. 14-17, a bone screw 64 of the type described above is adapted to be screwed into the descending pubic ramus 24 or 26, and a bone screw suture 250 having a suture body 252 extends from a suture end attached to the bone screw 64 to a suture free end 254. The suture body 252 is shaped with a series of suture fixation elements 258 projecting outward from the diameter of the suture body 252. Such suture fixation elements 258 may take any suitable form, e.g., cylindrical, spherical or the depicted generally conical shape. The suture fixation elements 258 are separated apart along suture body 254 by a distance that accommodates at least the thickness of urethral sling 30 and preferably the thickness of the urethral sling 30 and the thickness or length of a suture retainer that bears against the urethral sling 30. It will be understood that the depicted bone screw suture 250 may be provided with only one suture fixation element 258 suitably spaced from the bone screw 64 to receive and inhibit retraction of the suture retainer and/or the urethral sling 30 away from the descending pubic ramus 24 or 26 and toward the suture free end 254. The suture fixation element 258 that is in contact with the sling 30 and/or a suture retainer inhibits retraction of the suture retainer and/or the urethral sling 30 toward the suture free end 254.

Figure 15:
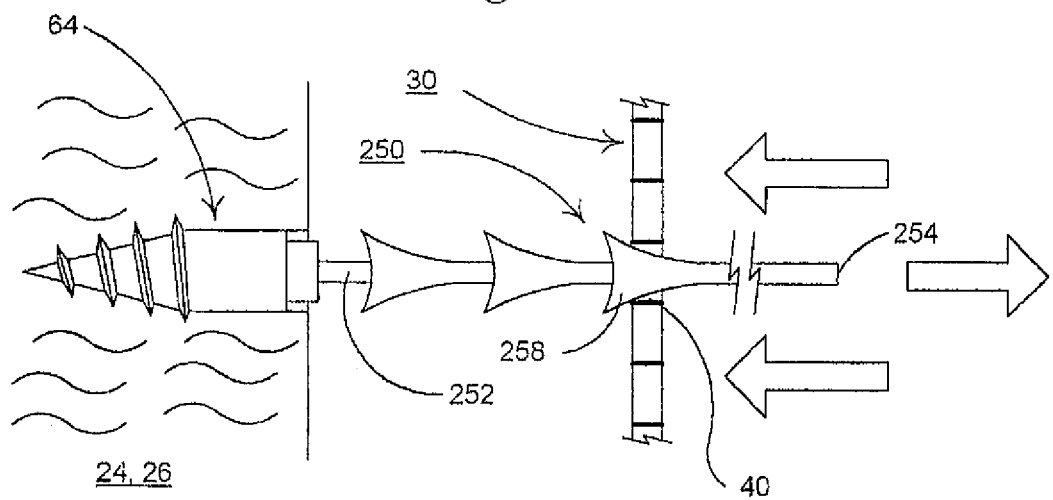
FIG. 15 is a side view illustrating the passage of the bone screw suture of the bone screw of FIG. 14 affixed to a descending pubic ramus through a mesh pore of the urethral sling and tensioning the urethral sling by progressively drawing barbed fixation elements through a mesh pore as a portion of the urethral sling is advanced toward the pubic bone surface.

Generally speaking, the suture fixation elements 258 are sized in maximum cross-section area to the selected sling opening, e.g., mesh pore 40, such that the suture fixation elements 258 can be barely passed through the sling opening. Thus, it is preferable that the suture fixation elements 258 have a relatively gradual ramp shape increasing in cross-section area from the suture body 252 to the maximum cross-section area closer to the bone screw 64. The ramp shape provides a sling opening expansion surface as the sling 30 is advanced from right to left over it as shown in FIG. 15. The ramp shape terminates with an abrupt transition back to the cross-section area of the suture body 252 to present a sling contact surface. The sling contact surface having a surface area exceeding the sling opening area is thereby provided to bear against the sling mesh or body to enhance retention of the sling. The depicted generally conical or arrowhead shape of the suture fixation elements 258 is simply one way of satisfying this preferred characteristic.

Consistent with the above-described methods, a plurality of bone screws, exemplified by the bone screw 64 of FIGS. 14-17, are affixed to the descending pubic rami 24 and 26. First, the suture 250 of each bone screw affixed to the descending pubic ramus 24 is inserted through a selected sling opening, e.g., a mesh pore 40 along a first end portion of the urethral sling 30 along sling end 32, and the first end portion is advanced over the sutures 250 against or proximate the descending pubic ramus 24. Preferably, a suture retainer is then interposed over or onto the bone screw suture body 252 to bear against the urethral sling 30 to retain it in position. Then, the suture 250 of each bone screw affixed to the descending pubic ramus 26 is inserted through a selected sling opening, e.g., a mesh pore 40 along a first end portion of the urethral sling 30 along sling end 34, and the first end portion is advanced over the sutures 250 against or proximate the descending pubic ramus 26. Preferably, a suture retainer is then interposed over or onto the bone screw suture body 252 to bear against the urethral sling 30 to retain it in position. Any of the above-described suture retainers 100, 160 and 200 may be interposed between the sling contact surface and the sling 30 by laterally passing the suture body 252 through a selected slot and into a suture retainer bore of the selected suture retainer.

An RPP test may be conducted, and one or more of the suture retainers may be adjusted along the length of the respective sutures 250 to adjust the sling tension if the test results are not satisfactory. The above-described steps may be repeated until the RPP test results are satisfactory. Finally, the suture free ends 254 may be trimmed and left untied or first tied with a simple small size knot and then trimmed at the discretion of the surgeon.

Figure 16:
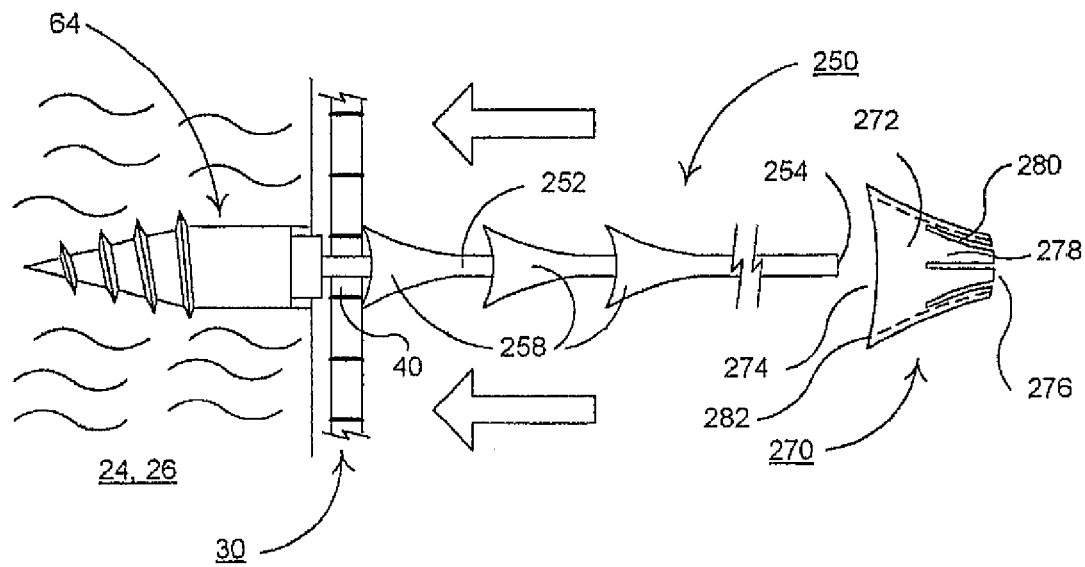
FIG. 16 is a side view illustrating the advancement of the portion of the urethral sling is proximate the pubic bone surface and the positioning of a further embodiment of a suture retainer over the free end of the bone screw suture.

An alternative exemplary suture retainer 270 is depicted in FIG. 16 that is advanced over the suture free end 254 and toward the urethral sling 30 over the suture fixation elements until the suture retainer 270 contacts the urethral sling 30. The suture retainer 270 is axially advanced into a retention position over the suture 250 and is configured to interlock with the suture fixation element 258 contacting the urethral sling 30 to bear against urethral sling 30 and to be maintained in the retention position.

Figure 17:
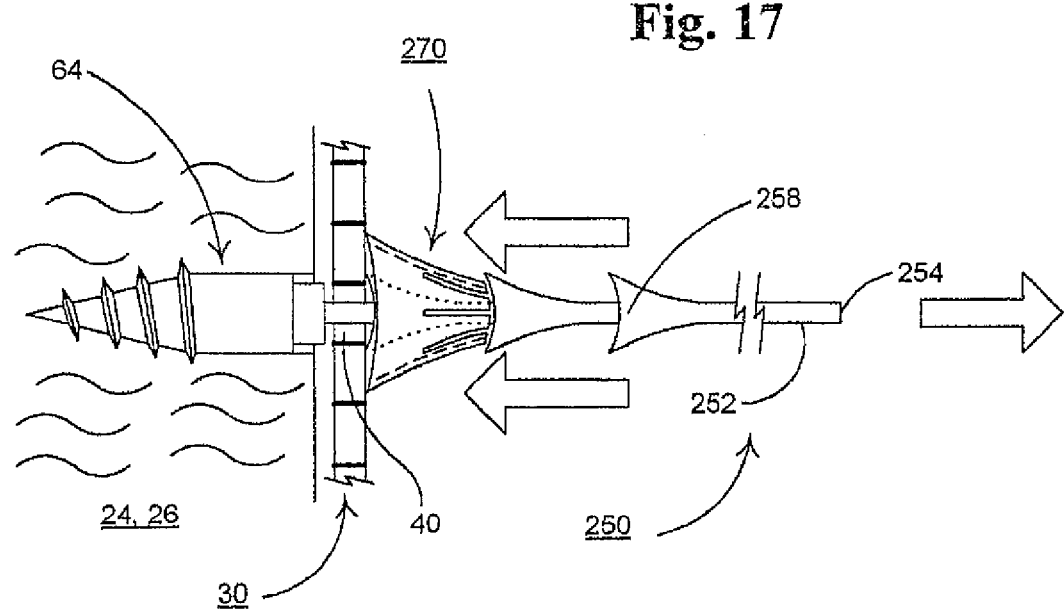
FIG. 17 is a side view illustrating the advancement of the suture retainer of FIG. 16 over the barbed fixation elements of the suture and against the urethral sling proximate the pubic bone surface thereby engaging the suture and retaining the mesh of the urethral sling proximate the pubic bone.

The suture retainer 270 has a generally annular, "cup-shaped" retainer body 272 defining and surrounding a central retainer bore 274 and having a body length equal to or exceeding the distance between adjacent suture fixation elements 258. The retainer body 272 extends between a minimum diameter or cross-section retainer end 276 that is adapted to be applied against a suture fixation element 258 and a maximum diameter or cross-section retainer end 282 that is adapted to be applied against the urethral sling 30 as shown in FIG. 17. The retainer body 272 is relatively thin walled and defines a retainer bore 274 extending between the retainer ends 276 and 282 that conforms with the shape of the suture fixation element, particularly the generally conical shape of suture fixation element 258. It will be understood that the maximum diameter or cross-section retainer end 282 may have any suitable diameter and may include an annular flat portion extending transversely to the axis of the retainer body 272.

Preferably, a plurality of resilient flaps 278 are provided between slots 280 through the retainer body 272. The resilient flaps 278 extend from the minimum diameter or cross-section retainer end 276 toward the maximum diameter or cross-section retainer end 282 to a diameter of the generally conical bore 274 corresponding generally to the maximum diameter of retainer end 282. Thus, the resilient flaps 278 are flexed outward to enable advancement of the suture retainer 270 over each suture fixation element 258. The resilient flaps 278 return to their resting shape with the retainer end 276 disposed against the abrupt sling contact surface end of an adjacent suture fixation element 258 when the retainer end 282 is applied against the urethral sling 30 as shown in FIG. 17.

It will be noted that the retainer 270 may also be modified to be applied over a constant diameter suture or suture pair, e.g., the suture pair 84 of bone screw 64 of FIG. 4, by suitably dimensioning the bore 274 to provide a frictional fit with the suture of suture pair 84. In this regard, the single and "multiple suture" retainers 300 and 310 depicted in FIGS. 18-20 are especially configured for over-the-suture application to the sutures 85 and 87 of the suture pair 84 of FIG. 4.

The single suture retainer 300 depicted in FIGS. 18 and 20 is formed of a generally planar circular or rectangular or oblong retainer body 302 having two retainer bores 306 and 308 extending through the retainer body 302 (or one retainer bore for both sutures or a single suture). The retainer bores 306 and 308 are smaller in cross-section area than the suture body cross-section area to provide an interference friction fit. The retainer bores 306 and 308 are preferably be bounded by resilient flaps that extend slightly out of the plane of the retainer body 302 created by slits similar to the flaps 278 and slits 280 of the suture retainer 270. For example, the retainer bores 306 and 308 are elongated and bounded by H-shape slits, although other bore and slit shapes, e.g., a starburst or radial slits from a circular bore, could be used. In this way, the retainer bores 306, 308, 320, 322, 324, 326, 328, 330 extend through the retainer body 304, 312 and are dimensioned and shaped to enable axial advancement of the retainers 300 and 310 over the suture into engagement with a portion of the urethral sling 30 and to resist axial retraction of the retainers 300 and 310 from engagement with the portion of the urethral sling 30.

In use, the bone screws 64, 66, and 68 may be screwed into the pubic bone of the descending pubic ramus 24, and the bone screws 70, 72, and 74 may be screwed into the pubic bone of the descending pubic ramus 26 as described above with respect to FIGS. 2 and 9. An end portion of the urethral sling 30 along sling end 32 is applied against or proximate the descending pubic ramus 24, as the suture pairs 84, 86, 88 are inserted through selected sling openings, e.g., mesh pores 40 depicted in FIG. 3. A first set of three suture retainers 300 are applied as shown in FIG. 20 to the suture pairs 84, 86, and 88 to retain, the urethral sling 30 proximate the descending pubic ramus 24.

The other sling end 34 of the urethral sling 30 is then drawn across the urethra toward the descending pubic ramus 26, and the suture pairs 90, 92, 94 are inserted through selected sling openings, e.g., mesh pores 40 depicted in FIG. 3, in an end portion of the urethral sling 30 along sling end 34. A second set of three suture retainers 300 are applied as shown in FIG. 20 to the suture pairs 90, 92, and 94 to retain the urethral sling 30 proximate the descending pubic ramus 26 and to thereby tension the portion of the urethral sling 30 extending across the urethral region.

An RPP test may be conducted, and one or more of the suture retainers 300 may be adjusted along the length of the respective suture pairs 84, 86, 88, 90, 92, and 94 to adjust the sling tension if the test results are not satisfactory. The above-described steps may be repeated until the RPP test results are satisfactory. Finally, the free ends of the suture pairs 84, 86, 88, 90, 92, and 94 may be trimmed and left untied or first tied with a simple small size knot and then trimmed at the discretion of the surgeon.

An embodiment of an exemplary, slitted bore "multiple suture" retainer 310 is depicted in FIGS. 19 and 20 that may constitute or resemble a plurality of the suture retainers 300 joined together end-to-end in an elongated array and may be employed instead of a plurality of suture retainers 300. One such suture retainer 310 would be applied along the urethral sling end 32 to engage the suture pairs 84, 86 and 88, and a further suture retainer 310 would be applied along the urethral sling end 34 to engage the suture pairs 90, 92, 94 in the manner of suture retainers 160 and 200 as described above with respect to FIG. 13. The sutures 85 and 87 of suture pair 84 may be passed through the bores 320 and 322, respectively, of a first suture retainer 310. Similarly, the sutures of the suture pairs 86 and 88 may be passed through the bores 324, 326 and 328, 330 of the first suture retainer 310. The sutures of suture pair 90 may be passed through the retainer bores 320, 322, the sutures of suture pair 92 may be passed through the retainer bores 324, 326, and the sutures of suture pair 90 may be passed through the retainer bores 328, 330 of a second suture retainer 310.

Again, it will be understood that the "multiple suture" suture retainer 310 may be formed with a greater number of spaced apart retainer bores like retainer bore 320, and the surgeon may select the retainer bores to receive the sutures of the suture pairs of the bone screws that are screwed into the pubic bones.

An RPP test may be conducted, and one or more of the suture retainers 310 may be adjusted along the length of the respective suture pairs 84, 86, 88, and suture pairs 90, 92, 94 to adjust the sling tension if the test results are not satisfactory. The above-described steps may be repeated until the RPP test results are satisfactory. Finally, the free ends of the suture pairs 84, 86, 88, 90, 92, and 94 may be trimmed and left untied or first tied with a simple small size knot and then trimmed at the discretion of the surgeon.

As noted above, the suture retainers 100, 160 and 200 may also be employed in conjunction with a shaped suture or sutures like shaped suture 250 depicted in FIGS. 14-17 having at least one enlarged suture fixation element 258 engaging the suture retainers 100, 160 and 200 against portions of the urethral sling. The selected suture retainer 100, 160 or 200 would be applied laterally to the suture body 252 between the enlarged end of the suture fixation element 258 and the urethral sling 30 to effect fixation in the manner of the suture retainer 270 as described above. The enlarged suture fixation element thereby enhances the fixation of the suture retainers 100, 160 and 200 with the suture pairs 84, 86, 88, 90, 92 and 94 shown in FIGS. 9 and 13.

Figure 21:
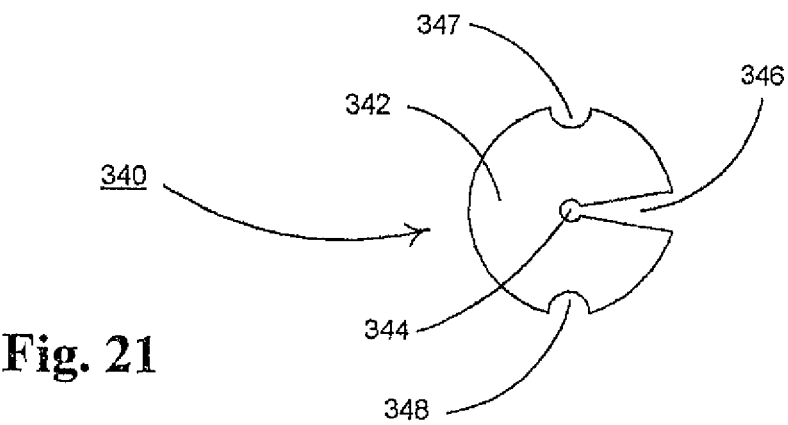
FIG. 21 is a top view of a further embodiment of a suture retainer employable with a single suture extending from a bone screw of the type depicted in FIG. 4.
Figure 22:
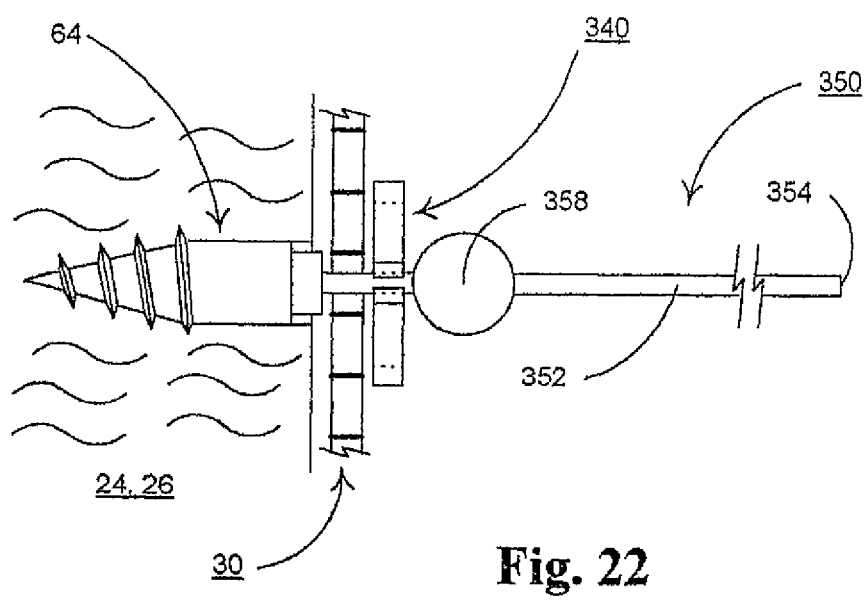
FIG. 22 is a side view illustrating the application of the suture retainer of FIG. 21 laterally between a barbed fixation element of a suture extending from a bone screw of the type depicted in FIG. 4 and against the urethral sling proximate the pubic bone surface thereby engaging the suture and retaining the mesh of the urethral sling proximate the pubic bone.

In this regard, a further single suture retainer 340 is depicted FIGS. 21 and 22 in cooperative relation with a single suture 350 having a single suture fixation element 358 disposed along the suture body 352 displaced from the suture free end 354 adjacent to the suture attached end with the bone screw 64. The suture fixation element 358 may or may not have a generally conical shape because the suture retainer 340 is applied laterally to the suture body 352 between the enlarged end of the suture fixation element 358 and the urethral sling 30 to effect fixation in the manner of the suture retainer 270 as described above but need not be applied over-the-suture as described above.

The suture retainer 340 is configured with a generally circular and substantially planar suture retainer body 342 having single retainer bore 344 open to the circumference of the retainer body 342 by a slit 346. It will be understood that a multiple suture retainer may alternatively be provided having an elongated substantially planar retainer body with a plurality of such bores and slits formed therein either regularly spaced apart or grouped in the manner of the suture retainer 160. In either case, the steps described above are followed to apply the suture retainer 340 laterally to frictionally engage the suture body 352 within the retainer bore 344 with the retainer body 342 interposed between the urethral sling 30 and the suture fixation element 358 as shown in FIG. 22.

Thus, in certain exemplary preferred embodiments, the bone screw sutures are extended through laterally extending slots into bores of the suture retainer into engagement with a portion of the urethral sling. In other exemplary preferred embodiments, the suture retainer is applied over the free ends and along bone screw sutures into engagement with a portion of the urethral sling.

The invention claimed is:

1. A surgical kit comprising:
   an implantable sling having opposed sling sides and extending between a first sling end and a second sling end, the sling comprising a sling opening formed through the sling adjacent the first sling end;
   an anchor;
   a first elongated anchor suture having a first end attached to the anchor and a second free end, wherein the first suture is passable through the sling opening to allow for movement of the sling along a length of the first suture relative to the anchor;
   a second elongated anchor suture having a first end attached to the anchor and a second free end, wherein the second suture is passable through the sling opening to allow for movement of the sling along a length of the second suture relative to the anchor;
   at least one single-piece suture retainer having a retainer body and at least first and second retainer bores through the retainer body, the first and second retainer bores positioned adjacent to each other across a width of the suture retainer, and sized and shaped to receive and frictionally engage the first and second sutures, respectively, adjacent the implantable sling to inhibit slippage of the first and second sutures, respectively, relative to the first and second retainer bores and to apply retentive force through the retainer body against the implantable sling to retain a portion of the implantable sling proximate a target location,
   wherein the retainer body further comprises first and second fixed slots extending from a retainer body edge to each of the first and second retainer bores, respectively, and dimensioned to enable lateral advancement of the suture retainer with respect to the first and second sutures to pass the first and second sutures through the first and second slots into the first and second retainer bores and to dispose the retainer into engagement with a portion of the sling,
   the retainer body defining a first recess defined on the retainer body edge at a first location, and a second recess defined on the retainer body edge at a second location; and
   a retainer installation and dispensing tool having a clamp having a first projection and a second projection, the first projection configured to engage with the first recess, the second projection configured to engage with the second recess.

2. The surgical kit of claim 1, wherein the first and second retainer bores are shaped to enable axial advancement of the retainer over the first and second sutures and into engagement with a portion of the implantable sling and to resist axial retraction of the retainer from engagement with the portion of the implantable sling.

3. The surgical kit of claim 1, wherein at least one of the first and second sutures has a variable suture cross-sectional area and comprises a suture body extending from the suture anchor to a suture free end, the suture body having a retention element extending outwardly from the suture body.

4. The surgical kit of claim 3, wherein the first and second slots are dimensioned to enable lateral advancement of the retainer with respect to the first and second sutures to pass the first and second sutures through the first and second slots into the first and second retainer bores and to dispose the retainer into engagement with and between the retention element and the portion of the implantable sling.

5. The surgical kit of claim 3, wherein the first and second retainer bores extend through the retainer body and are dimensioned to enable axial advancement of the retainer over the first and second sutures into engagement with the portion of the implantable sling.

6. The surgical kit of claim 3, wherein the retainer body extends from a first body end to a second body end, wherein each of the first and second retainer bores extend from a first bore diameter at the first body end sufficient to receive the retention element to a second bore diameter at the second body end smaller than the first bore diameter, and wherein the retainer body is expandable at the second body end to expand the second bore diameter to pass the retention element through the retainer bore.

7. The surgical kit of claim 6, wherein the retention element is shaped to expand the second bore diameter as the retainer body is advanced over the retention element and to allow contraction of the second bore diameter upon passage of the retainer body over the retention element.

8. The surgical kit of claim 3, wherein the retention element is tapered down in cross-sectional area from a location spaced from the first end of the first and second sutures toward the suture free ends.

9. The surgical kit of claim 8, wherein the retention element includes a conical shape.

10. The surgical kit of claim 8, wherein the retention element is a first retention element, and the suture body includes a second retention element, the first retention element and the second retention element being spaced from each other along the length of the suture by a first distance, wherein the first distance is at least as large as a combination of a thickness of the sling and a thickness of the suture retainer.

11. The surgical kit of claim 1, wherein the retainer installation and dispensing tool includes a tab extending from the clamp, the tab configured to be gripped by an operator, the tab having a width smaller than a width of the clamp.

12. A surgical kit comprising:
an implantable sling having opposed sling sides and extending between a first sling end portion and a second sling end portion, the sling comprising a first set of sling openings disposed on the first sling end portion and a second set of sling openings disposed on the second sling end portion;
a plurality of anchors;
a plurality of pairs of sutures, each pair of sutures includes first ends attached to a different anchor of the plurality of anchors and suture free ends, wherein each suture is passable through one of the sling openings to allow for movement of the sling along a length of the suture relative to the anchor to which it is attached;
a first suture retainer including a first retainer body and a first retainer cover, the first retainer body including a plurality of pairs of retainer bores, each pair of retainer bores being sized and shaped to receive a different pair of sutures that extend from the first set of openings, the first retainer body configured to be coupled to the first retainer cover to entrap the sutures that extend from the first set of openings;
a second suture retainer including a second retainer body, and a second retainer cover, the second retainer body including a plurality of pairs of retainer bores, each pair of retainer bores of the second retainer body being sized and shaped to receive a different pair of sutures that extend from the second set of openings, second retainer body configured to be coupled to the second retainer cover to entrap the sutures that extend from the second set of openings.

13. The surgical kit of claim 12, wherein the first retainer body is coupled to the first retainer cover based on a snap fit.

14. The surgical kit of claim 12, wherein the first retainer body is movably coupled to the first retainer cover.

* * * * *